United States Patent [19]

Yen et al.

[11] Patent Number: 5,171,684

[45] Date of Patent: * Dec. 15, 1992

[54] **BIOCONVERSIONS CATALYZED BY THE TOLUENE MONOOXYGENASE OF *PSEUDOMANAS MENDOCINA* KR-1**

[75] Inventors: Kwang-Mu Yen, Thousand Oaks; Lawrence M. Blatt, West Hills; Michael R. Karl, Port Hueneme, all of Calif.

[73] Assignee: Amgen Inc., Thousand Oaks, Calif.

[ * ] Notice: The portion of the term of this patent subsequent to May 21, 2008 has been disclaimed.

[21] Appl. No.: 590,374

[22] Filed: Sep. 28, 1990

Related U.S. Application Data

[63] Continuation-in-part of Ser. No. 177,631, Apr. 5, 1988, Pat. No. 5,017,495.

[51] Int. Cl.$^5$ .................. C12P 21/00; C12P 19/34; C12N 15/00; C12N 1/21; C12N 1/16; C12N 1/18; C07K 3/00; C07H 15/12
[52] U.S. Cl. .................. 435/252.3; 435/91; 435/172.3; 435/320.1; 435/252.33; 435/255; 435/256; 435/68.1; 536/27; 530/350; 935/9; 935/29; 935/58; 935/56; 935/60; 935/63; 935/82

[58] Field of Search .................. 435/68.1, 91, 172.3, 435/320.1, 252.3, 252.33, 255, 256; 536/27; 530/350; 935/9, 29, 38, 56, 60, 73, 82

[56] References Cited

PUBLICATIONS

White, G. M., PhD Thesis Univ Texas at Austin Dissitation Abstracts International p. 1861, vol. 47/05-B (1986).

*Primary Examiner*—Joan Ellis
*Attorney, Agent, or Firm*—Allegretti & Witcoff

[57] ABSTRACT

Disclosed and claimed are toluene monooxygenase (TMO) gene sequences from *Pseudomonas mendocina* KR-1, TMO proteins encoded by these sequences, recombinant plasmids containing such sequences, and microorganism host cells containing such plasmids. A five-gene and six-gene TMO gene cluster encode proteins that are useful in a variety of bioconversions. In particular, the TMO gene cluster is useful for the preparation of p-hydroxyphenylacetic acid and indigo. In addition, the TMO gene cluster is useful for the degradative bioconversion of toxic compounds, such as trichloroethylene.

22 Claims, 11 Drawing Sheets

```
  1 AAGCTTTAAACCCCACAGGCACGGAGAACAAGAATATGGCGATGCACCCACGTAAAGACTGGTATGAACTGACAGGGCGACAAATTGGACACCTAGCT
                                   (tmoA) M A M H P R K D W Y E L T R T N W T P S Y 101 ATGTTACCGAAGAGACAGCTTTTCCCAGAGCGGATGTCCGGTCATATGGGGTATCCCGCTGGAAAAATGGAAAGCTATGATGAGCCTATAAGACATCCTA
    V T E E Q L F P E R M S G H M G I P L E K W E S Y D E P Y K T S Y 201 TCCGGAGTACGTAAGTATCCAACGTGAAAAGGATGCAGGTGCTTATTCGGTGAAGGCGCACTTGAGCGTGCAAAAATTTATGAACTCTGACCCAGGT
    P E Y V S I Q R E K D A G A Y S V K A A L E R A K I Y E N S D P G 301 TGGATCAGCACTTTGAAATCCATTACGGCGCCATCGCAGTTGGTGAATATGCAGCGTAACCGGTGAAGGTCGTATGGCCGTTTTCAAAGCACCGG
    W I S T L K S H Y G A I A V G E Y A A V T G E G R M A R F S K A P G 401 GAAATCGCAACAATGGCTACGTTGGCATGATGATGAACTGCGCCATGGCCAGTTACAGCTGTGTTTTCCCGCATGAATACTGTAAGAAGGATCGCCAGTT
    N R N M A T F G H M D E L R H G Q L F F P H E Y C K K D R Q F 501 TGATTGGGCATGGCGGGGCTATCACAGTAACGAATGGGCAGCCATTGCTGCAAAGCATTTCTTTGATGACATCATTACCGGACGTGATGCGATCAGCGTT
    D W A W R A Y H S N E W A A I A K H F F D D I I T G R D A I S V 601 GCGGATCATGTTGACGTTTCATTCGAAACCGGCTTCACCAACATGCAGTTCTTGGGGGCCAGATGCCGCAGAAGCAGGTGACTACACGTTTGCAA
    A I M L T F S F E T G F T N M Q F L G L A A D A A E A G D Y T F A N 701 ACCTGATCATGTCCCAGCATTCAAACGATGAGTCGCGTCATGCACAACAGGGCGGGCCATTACAGTGCTGATCGAAAACGAAAAAGAGAAGAAGCCCA
    L I S S I Q T D E S R H Q Q G G P A L Q L L I E N G K R E E A Q
```

FIG. 5A

```
801  AAGAAAGTCGACATGGCAATTTGGCGTGCCTCTATTTGCCGTCTATGGATTACTACACGGGCCGGTTGGAGGACCGCAGCCAG
      K  K  V  D  M  A  I  W  R  A  V  R  L  F  A  V  L  T  G  P  V  M  D  Y  Y  T  P  L  E  D  R  S  Q

901  TCATTCAAGGAGTTTATGTACGAGTGGATCATCGGACAGTTCGAACGCTCGTTGATAGATCTGGGTCTTGACAAGCCCTGGTACTGGGATCTATTCCTCA
      S  F  K  E  F  M  Y  E  W  I  I  G  Q  F  E  R  S  L  I  D  L  G  L  D  K  P  W  Y  W  D  L  F  L  K

1001 AGGATATTGATGAGCTTCACCATAGTTATCACATGGGTGTGTTTGGACTGGCGTACAACCGCTTGGTGGAACCCTGCTGCCGGGGTCACTCCTGAGGAGCG
      D  I  D  E  L  H  H  S  Y  H  M  G  V  L  D  W  R  T  T  A  W  N  P  A  A  G  V  T  P  E  E  R

1101 TGACTGGCTGGAAGAAAAGTATCCAGGATGGAATAAACGTTGGGGTCGTTGCTGCTGGATGTGATCACCGAAAACGTTCTCAATGACCGTATGGATCTTGTC
      D  W  L  E  E  K  Y  P  G  W  N  K  R  W  G  R  C  W  D  V  I  T  E  N  V  L  N  D  R  M  D  L  V

1201 TCTCCAGAAACCTTGCCAGCTGTGCAACATGAGCCAGATACCGCTGGTAGGTGTTCCTGGTGATGACTGGAATATCGAAGTTTTCAGTCTTGAGCACA
      S  P  E  T  L  P  S  V  C  N  M  S  Q  I  P  L  V  G  V  P  G  D  D  W  N  I  E  V  F  S  L  E  H  N

1301 ATGGGGTCTTTATCATTTGGCTCTGAAGTGGATCGCTCGAAGTGGATGTTCAGTATGCAGATCCGTTCAGTATATGATATGTCGACCGCTTCCT
      G  R  L  Y  H  F  G  S  E  V  D  R  W  V  F  Q  Q  D  P  V  Q  Y  Q  N  H  M  N  I  V  D  R  F  L

1401 CGCAGGTCAGATACAGCCGATGACTTTGGAAGGTGCCCTCAATCTATTGAAGAGATGGGCAAAGACGCCACGACTTTGCATGG
      A  G  Q  I  Q  P  M  T  L  E  G  A  L  K  Y  M  G  F  Q  S  I  E  E  M  G  K  D  A  H  D  F  A  W

1501 GCTGACAAGTGCAAGCCTGCTATGAAGAAAATCGGCCTGATAAATTGAGGAATAGAAAATGTCGGCATTTCCAGTTCACGCAGCGTTTGAAAAAGATTTCT
      A  D  K  C  K  P  A  M  K  K  S  A  *                 (tmoB) M  S  A  F  P  V  H  A  A  F  E  K  D  F  L
```

FIG. 5B

```
1601 TGGTTCAACTGGTAGTGGTGGATTAAATGATTCCATGGACCAGGTAGGCGGAGAAAGTGCCTACCATTGTGTTAATCGTCGTGTGCTCCTCGTGAAGG
      V  Q  L  V  V  V  D  L  N  D  S  M  D  Q  V  A  E  K  V  A  Y  H  C  V  N  R  R  V  A  P  R  E  G

1701 TGTCATGCGGGTTCGAAAGATAGATCAACTGAGTCTTTCCACGGATATGACCATAGTCGAGAGCGGCCTTAACCAACTGAAGTGATCGATGTGGTA
      V  M  R  V  R  K  H  R  S  T  E  L  F  P  R  D  M  T  I  A  E  S  G  L  N  P  T  E  V  I  D  V  V

1801 TTCGAGGAGTAGCGAAAATGAGCTTTGAAAAATCTGTTCCCTCGACGATATCTGGGTAGGCGAATGAGACTTTCGAGACGTCCGATGGTACCGAAGT
      F  E  E  *(tmoC) M  S  F  E  K  I  C  S  L  D  D  I  W  V  G  E  M  E  T  F  F  E  T  S  D  G  T  E  V 1901 CTTAATCGTCAACAGTGAAGAGCATGAAGTGAAGGCCTACCAGGCGATGTGCCCCCATCAGGAGATTCTGTATCTGAAGGTAGCTACGAAGGTGGAGTA
      L  I  V  N  S  E  E  H  G  V  K  A  Y  Q  A  M  C  P  H  Q  E  I  L  L  S  E  G  S  Y  E  G  G  V 2001 ATTACATGCCGGCTCACCTATGGACCTTCAATGACGGAACCATGGCATCAACCAGATGACTGTTGTCTTGCCACCAGAATATCCTGTAGAGGTAAAG
      I  T  C  R  A  H  L  W  T  F  N  D  G  T  G  H  G  I  N  P  D  D  C  L  A  E  Y  P  V  E  V  K  G 2101 GCGATGATATTTACGTCAGTACAAAAGGCATTTTACGGAATAAGGCACACAGCTAAACTGCGCTAGTGTTAAATCCCACATCAGGGAAGCGGCTGGGA
      D  D  I  Y  V  S  T  K  G  I  L  P  N  K  A  H  S  *

2201 AAAGAAGGATAATGTGATGAGCACATTGGCTGATCAGGCTTTACATAACAATAACGTTGGACCGATTATCCGTCGTGGTGATCTCGTGGAACCAGTGATT
      (tmoD) M  S  T  L  A  D  Q  A  L  H  N  N  N  V  G  P  I  I  R  A  G  D  L  V  E  P  V  I 2301 GAAACAGCTGAAATCGAATAATCCGGGAAAAGAGATCACAGTTGAAGATAGGCGGGTTATGTACGGATCAGGAAGGCGAACTGATATTGACTCGAA
      E  T  A  E  I  D  N  P  G  K  E  I  T  V  E  D  R  R  A  Y  V  R  I  A  E  G  E  L  I  L  T  R  K 2401 AAACCTTGGAAGAGCAGTTGGGTCGCCCGTTCAACATGCAGGAACTAGAAATCAATCTGGCTCCTTTGCAGGACAGATCAAGCCGACGAAGACCAGAT
      T  L  E  E  Q  L  G  R  P  F  N  M  Q  E  L  E  I  N  L  A  S  F  A  G  Q  I  Q  A  D  E  D  Q  I
```

FIG. 5C

```
2501  TCGCTTCTACTTTGATAAAACCATGTAAGGAGGGCACCATGAGCTTTGAATCCAAGAAAACCGATGCTACATGGAGCCACTGGCCGAAATGAGAAAGAA
      R  F  Y  F  D  K  T  M  *      (tmoE) M  S  F  E  S  K  K  P  M  R  T  W  S  H  L  A  E  M  R  K  K 2601  GCCAAGTGAGTACGATATTGTCTCACGCAAGCTTCACTACAGTACCAACAATCCGATTCACCCTGGGAGCTGAGCCCGATAGCCAATGAATCTGTGG
      P  S  E  Y  D  I  V  S  R  K  L  H  Y  S  T  N  N  P  D  S  P  W  E  L  S  P  D  S  P  M  N  L  W 2701  TACAAGCAGTACCGTAACGCCATCGGCCATTGAAACACGATAACTGGATGCTTTTACTGATCCTGACCAACTTGTATACCGCCACTACAACCTGATGCAGG
      Y  K  Q  Y  R  N  A  S  P  L  K  H  D  N  W  D  A  F  T  D  P  D  Q  L  V  Y  R  T  Y  N  L  M  Q  D 2801  ATGGTCAGGAATCTTATGTGCAGAGTCTGTTCGATCAATTCAATGAGCGGGAACATGACCAAATGGTGCGGGAGGCTGGGAGCACAATGGCCCGCTG
      G  Q  E  S  Y  V  Q  S  L  F  D  Q  F  N  E  R  E  H  D  Q  M  V  R  E  G  W  E  H  T  M  A  R  C 2901  TTATTCCCGTTGCGCTATCTGTTCCACTGCCTGCAGATGTCTCAGCAGATGCCGGCCTATGTTCAGCAGATGGCGCCCGGAGCACAATCTCAAATTGCTGCATCCTT
      Y  S  P  L  R  Y  L  F  H  C  L  Q  M  S  S  A  Y  V  Q  Q  M  A  P  A  S  T  I  S  N  C  C  I  L 3001  CAAACTGCTGACAGCCTGCGATGGTTGACGCACGACACACCGCCTACCGACCGACAACTCAGTCTTCTTACTTATCCGATGCTGGTTAGGTGAGCAGGAGCAGGAG
      Q  T  A  D  S  L  R  W  L  T  H  T  A  Y  R  T  H  E  L  S  L  T  Y  P  D  A  G  L  G  E  H  E  R  E 3101  AACTGTGGGAGAAAGAGCCGGGTTGGCAGGGGCTGCGTGAATTGATGGAGAAGCAACTAACTGCTTTGATTGGGAGAGGCTTTGTCAGTCTAAATTT
      L  W  E  K  E  P  G  W  Q  G  L  R  E  L  M  E  K  Q  L  T  A  F  D  W  G  E  A  F  V  S  L  N  L 3201  GGTGGTCAAGCCAATGATTGTCGAGAGTATTTTCAAACCACTGCAGCAGCAAGCATGGAAAATAACGATACCTTGCTTCCTCGTTGATTGACAGTCAG
      V  V  K  P  M  I  V  E  S  I  F  K  P  L  Q  Q  Q  A  W  E  N  N  D  T  L  L  P  L  L  I  D  S  Q
```

FIG. 5D

```
3301  CTGAAAGATGCCGAGGTCATAGTCGTTGGTCGAAAGCACTTGTAAAACATGGCTGGAAATCCCGATAATCACGCTGTAATTGAAGGTTGGATTGAAA
       L  K  D  A  E  R  H  S  R  W  S  K  A  L  V  K  H  A  L  E  N  P  D  N  H  A  V  I  E  G  W  I  E  K

3401  AGTGGGGCCCCTTGGCTGACAGGGCAGCTGAAGCTTACCTGAGTATGCTATCTGAGTATGCTCAATATCTTGAGGCGTAGTACCTCATTGAG
       W  R  P  L  A  D  R  A  A  E  A  Y  L  S  M  L  S  S  D  I  L  H  A  Q  Y  L  E  R  S  T  S  L  R

3501  GGCATCCATACTTACGGTCTGATTACGGCCCGTTGGGTCTCCCTTCGGCATTGCTGAAGGGGCTTTTTAGAGACGTTATCTATG
       A  S  I  L  T  V  *                                                    (tmoF) M 3601  TTCAATATTCAATCGGATGATCTCCTGCACCATTTTGAGGCGGATAGTAATGACACTCTACTAGTGCTGCTCTACGTGCTGAATTGGTATTTCCATATG
       F  N  I  Q  S  D  D  L  L  H  F  E  A  D  S  N  D  T  L  L  S  A  A  L  R  A  E  L  V  F  P  Y  E 3701  AGTGTAACTCAGGAGGGTGCGGCCATGTAAGATCGAGCTGCTTGAGGAGAGGTCTCTAACCTATGGCCTGATGCACCAGGATTAGCCCCGTGAACT
       C  N  S  G  G  C  G  A  C  K  I  E  L  L  E  G  E  V  S  N  L  W  P  D  A  P  G  L  A  A  R  E  L 3801  CCGTAAGAATCGTTTTGGCGTGCCAGTGCAAACCATTATCCGACCTCAAATTAAGGTCATTAACCGTGCGAGGACGTGCTTCACATCCCCCCAAA
       R  K  N  R  F  L  A  C  Q  C  K  P  L  S  D  L  K  I  K  V  I  N  R  A  E  G  R  A  S  H  P  P  K 3901  CGTTTCTCGACTCGAGTAGTTAGTAAGGCGTTCCTGAGTGTTTGAGCTGGAACAGAAAGTGGTGTTTCACCAGGCAAT
       R  F  S  T  R  V  V  S  K  R  F  L  S  D  E  M  F  E  L  R  L  E  A  E  Q  K  V  V  F  S  P  G  Q  Y 4001  ATTTTATGGTTGACGTGCCTGAACTCGGCACCAGAGCATACTCCGGGCAAACCTGTTGATGAAACACTAACGCTGATCGTAAAGCAGTGCCGAA
       F  M  V  D  V  P  E  L  G  T  R  A  Y  S  A  A  N  P  V  D  G  N  T  L  T  L  I  V  K  A  V  P  N
```

FIG. 5E

```
4101  TGGGAAGGTATCCTGGCCACTCGCAAATGAAACTATTGAAACACTTCAGTATTAAAAACTGCGATGAAACTCAA
      G  K  V  S  C  A  L  A  N  E  T  I  E  T  L  Q  L  D  G  P  Y  G  L  S  V  L  K  T  A  D  E  T  Q

4201  TCCGTCTTTATCGCTGGGGGTCAGTGTCAGGATGTGTCGATGCCGATGGTGTCGATTACGGTGTTTACG
      S  V  F  I  A  G  G  S  G  I  A  P  M  V  S  M  V  N  T  L  I  A  Q  G  Y  E  K  P  I  T  V  F  Y  G

4301  GTTCACGGCTAGAAGCTGAACTGGAAGCGGCCGAAACCCTGTTTGGGTGGAAAGAAAATTTAAAACTGATTAATGTGTCGTCGAGCGTGGTGGGTAACTC
      S  R  L  E  A  E  L  E  A  A  E  T  L  F  G  W  K  E  N  L  K  L  I  N  V  S  S  S  V  V  G  N  S

4401  GGAGAAAGTATCCGACCGGTTATGTCCATGAGATAATTCCTGAATACATGGAGGGCCTAGGTGCCGAGTTCTATCTGTGCGGCCCGCCGCAGATG
      E  K  K  Y  P  T  G  Y  V  H  E  I  I  P  E  Y  M  E  G  L  L  G  A  E  F  Y  L  C  G  P  P  Q  M

4501  ATTAACTCCGTCCAGAAGTTGCTTATGATTGAAAATAAGTACCGTTCGAAGCGATTCATTTGATAGGTTCTTTTAAATTAATAAGCAATAGTTGGTT
      I  N  S  V  Q  K  L  L  M  I  E  N  K  V  P  F  E  A  I  H  F  D  R  F  F  *

4601  TTAGTAGAATTTTCAGTGGCGTAATGTCGGGCTAAGGAACTCCGATAAGCCTGCACCAATACGGCAGTAGCCTGTTCAATGTGTTCTCAGGCAGCCG

4701  CAGCCAGCTGATTCGTCCAGTAGCCCGGG  4729
```

FIG. 5F

```
         1
NahA_b   MT-EKWIEAV ALSDIPEGDV LGV-TVEG-K E--LALYEVE GEIY--AT-D
         ||  |||      ::          :||         :  :       :
TmoC     MSFEK-ICS- -LDDIWVGEM ETFETSDG-T E-VLIV-NSE -EHGVKAYQA
           :  :       :  :       :  :      :  :   :       :
BdoB     MTWT-YILRQ --SDLPPGEM QRY----EGGS EPVM-VCNVD GEFF--AVQD 51                                                  100
NahA_b   NLCTHGAARM SDG-YLEGRE I-ECPLHQGR FDVCTGRALC APVTENIKTY
         ::|  |||     :|::        |  ||    |: | ::::
TmoC     -MCPHQEILL SEGSYEGGV- IT--CRAHLWT FNDGTGHGIN -PDDCCLAEY
          :  ||||     : |         |  ::|    | | ||
BdoB     -TCTHGDWAL SEG-YLDGD- VVECTLHFGK FCVRTGKVKA LPACKPIKVY 101              126
NahA_b   AV--KIENLR VMIDLS-GEF ------
         :|        :  :
TmoC     PVEVK--GDD IYVST-KGIL PNKAHS
         |:          |  :
BdoB     PI--KIEGDE VHVDLDNGEL K-----
```

FIG. 6

BIOCONVERSIONS CATALYZED BY THE TOLUENE MONOOXYGENASE OF *PSEUDOMANAS MENDOCINA* KR-1

BACKGROUND OF THE INVENTION

This application is a continuation-in-part of U.S. Ser. No. 177,631 filed Apr. 5, 1988, now U.S. Pat. No. 5,017,415, issued May 21, 1991, which is hereby incorporated by reference.

The present invention is directed to the use of recombinant DNA techniques to confer upon microorganism host cells the capacity for selected bioconversions. More specifically, the invention is directed to the cloning of toluene monooxygenase genes from a newly isolated and characterized *Pseudomonas* strain, *Pseudomonas mendocina* KR-1. The present invention provides genetically engineered plasmids that allow production of toluene monooxygenase enzymes and proteins in a variety of Gram-negative bacteria in the absence of a toxic inducer, and provides more efficient means of conducting bioconversions dependent on this enzyme system.

A bacterial strain identified as *Pseudomonas mendocina* KR-1 (PmKR1) was isolated by Richardson and Gibson from an algal-mat taken from a fresh water lake. Whited, Ph.D. Dissertation, The University of Texas at Austin, Library Reference No. W586 (1986). PmKR1 utilizes toluene as a sole carbon and energy source. Other bacterial strains have been isolated and described which metabolize or degrade toluene, including *Pseudomonas putida* mt-2 (Pp mt-2) (Williams and Murray, J. Bacteriol. 120: 416-423 (1974) and *Pseudomonas putida* PpF1 (PpF1) (Gibson. et al. Biochemistry 9:1626-1630 (1970)). In addition, a bacterial strain designated G4, isolated from a waste treatment lagoon, can metabolize toluene (Shields et al., App. Environ. Microbiol. 55: 1624-1629 (1989)). However, the genes, the enzymes and the pathways for toluene metabolism in these various bacterial strains are distinct and non-overlapping.

The catabolic pathway for the degradation of toluene by Pp mt-2 has been designated TOL. The genes for the TOL pathway are encoded on isofunctional catabolic plasmids found in certain strains of Pseudomonas. The reference plasmid for the TOL degradative pathway is pWWO originally isolated from Pp mt-2. The genetics and biochemistry of the TOL pathway are well described. Kunz and Chapman, J. Bacteriol. 146:179-191 (1981); Williams and Murray, J. Bacteriol. 120:416-423 (1974); Williams and Worsey, J. Bacteriol. 125:818-828 (1976); Worsey and Williams, J. Bacteriol. 124:7-13 (1975); Murray, et al., Eur. J. Biochem. 28.301-310 (1972). In particular, detailed studies of the organization and regulation of the TOL pathway genes of plasmid pWWO have been performed. Franklin, et al., Proc. Natl. Acad. Sci. USA 78: 7458-62 (1981); Spooner et al., J. Gen. Microbiol. 132: 1347-58 (1986); Spooner, et al., J. Bacteriol. 169: 3581-86 (1987); Inouye et al., J. Bacteriol. 169: 3587-92 (1987); Inouye et al., Gene 66: 301-306 (1988). A brief summary of the TOL pathway is as follows: initial attack of toluene is at the methyl group which undergoes successive oxidations to form benzoic acid, which is further oxidized by formation of a cis-carboxylic acid diol, which is oxidized to form catechol, which is then degraded by enzymes of a meta cleavage pathway to acetaldehyde and pyruvate.

A second catabolic pathway for the degradation of toluene by PpF1 has been established and designated TOD. In contrast to the TOL pathway, the genes for the TOD pathway are located on the bacterial chromosome and are not plasmid-encoded. Finette, et al., J. Bacteriol. 160:1003-1009 (1984); Finette, Ph.D. Dissertation, The University of Texas at Austin, Library Reference No. F494 (1984). The genetics and biochemistry of the TOD pathway has been studied by Finette, et al. (supra); Finette (supra); Gibson, et al. Biochemistry 9:1626-1630 (1970); Kobal, et al., J. Am. Chem. Soc. 95:4420-4421 (1973); Ziffer, et al., J. Am. Chem. Soc. 95.4048-4049 (1973); Dagley, et al., Nature 202:775-778 (1964); Gibson, et al., Biochemistry 7:2653-2662 (1968). A brief summary of the TOD pathway is as follows: the initial attack of toluene is by a dioxygenase enzyme system to form(+)-cis-1(S),2(R)-dihydroxy-3-methylcyclohexa-3,5-diene(cis-toluene dihydrodiol) which is oxidized to 3-methylcatechol which is further degraded by enzymes of a meta cleavage pathway. Zylstra and Gibson, J. Biol. Chem. 264: 14940-46 (1989) and McCombie, Abstr. Annu. Meet. Am. Soc. Microbiol. K53: 155 (1984) have reported the cloning and sequencing of the tod genes which encode the first three enzymes in the TOD pathway.

A third catabolic pathway for the degradation of toluene has been recently identified in PmKR1. It has been found that PmKR1 catabolizes toluene by a novel pathway which is completely different than either of the two pathways described above. Richardson and Gibson, Abstr. Annu. Meet. Am. Soc. Microbiol. K54:156 (1984). The catabolic pathway for the degradation of toluene by PmKR1 has been designated TMO, because the first step in the pathway is catalyzed by a unique enzyme complex, toluene monooxygenase. The biochemistry of the partially purified enzymes and proteins of this pathway has been recently studied by Whited, Ph.D. Dissertation, The University of Texas at Austin, Library Reference No. W586 (1986).

More recently, a toluene catabolic pathway, apparently distinct from the three above-described pathways, has been described in the trichloroethylene-degrading bacterium G4 by Shields et al., App. Environ. Microbiol. 55: 1624-1629 (1989). The bacterial strain designated G4 was isolated from a waste treatment lagoon. Strain G4 is uncharacterized with respect to genus and species. The toluene pathway of G4 appears to involve dihydroxylations of the aromatic ring by two monooxygenations, first ortho and then meta. The enzymes involved in these reactions have not been isolated and studied, and therefore remain completely uncharacterized.

The steps of the TMO pathway as outlined by Whited (supra) are diagrammed in FIG. 1. In the initial step toluene is oxidized to p-cresol, followed by methyl group oxidation to form p-hydroxybenzoate, followed by hydroxylation to protocatechuate and subsequent ortho ring cleavage. In the first step of the TMO pathway, toluene is converted by toluene monooxygenase to p-cresol. PmKR1 elaborates a unique multicomponent enzyme system which catalyzes this first step monooxygenase reaction. The implications of the teachings of Whited, (supra), suggest that at least three protein components may be involved: component a (possibly NADH oxidoreductase, molecular weight unknown), component b (possibly an oxygenase, at least 2 subunits) and component c (red-brown, probably ferredoxin, 23,000d.).

Despite beginning biochemical studies of the enzymes and proteins of the TMO pathway (Whited, supra) and beginning genetic studies (Yen et al. Abstract, University of Geneva EMBO Workshop, Aug. 31-Sep. 4. 1986), the art has not been provided with information regarding the genes encoding the enzymes and proteins of the toluene monooxygenase system in PmKR1 or the usefulness of such genes and gene products in certain microbial bioconversions. The art has also not been provided with microorganism host cells harboring novel recombinant plasmids containing PmKR1 toluene monooxygenase genes, in which induction of the toluene monooxygenase genes does not involve use of toxic compounds or simultaneous induction of other undesirable genes and in which some of the microorganism host cells harboring such recombinant plasmids under certain conditions express toluene monooxygenase enzyme activity at levels that equal, or under certain assay conditions, exceed the activity of wildtype PmKR1 cells.

SUMMARY OF THE INVENTION

The present invention provides novel gene segments, biologically functional plasmids and recombinant plasmids, and microorganism host cells, all of which contain the PmKR1 toluene monooxygenase genes. The present invention further provides a microorganism host cell harboring a novel recombinant plasmid containing PmKR1 toluene monooxygenase genes, in which synthesis of only toluene monooxygenase but not other undesirable enzymes can be induced specifically with an innocuous and inexpensive inducer and at levels that equal or, under certain conditions, exceed the activity of wildtype PmKR1 cells. In addition, the present invention provides a method for using transformed microorganism host cells containing the PmKR1 toluene monooxygenase genes in microbial bioconversions. Thus, the present invention provides microorganisms genetically engineered to produce toluene monooxygenase enzymes and proteins specifically and under innocuous conditions and therefore provides a more efficient means of conducting bioconversions with this enzyme system.

The present invention encompasses a biologically functional plasmid derived from PmKR1 containing toluene monooxygenase genes. This plasmid (designated pAUT1) can be transferred by conjugation to a microorganism host cell lacking the toluene monooxygenase gene system and thus unable to convert toluene to p-cresol. In a particularly preferred embodiment of the present invention, the microorganism host cell for the pAUT1 plasmid is *Pseudomonas putida KT*2440.

The present invention also encompasses the toluene monooxygenase genes which have been isolated as various DNA gene segments from PmKR1 and cloned into a suitable, autonomously-replicating plasmid vector, resulting in a series of recombinant plasmids each of which contains a toluene monooxygenase gene segment. Each such recombinant plasmid is biologically functional and can be used to transform a microorganism host cell, conferring on the microorganism host cell the ability to convert toluene to p-cresol.

The present invention further encompasses a series of such transformed microorganism host cells. In a preferred embodiment of the present invention, the microorganism host cell is *E. coli* HB101, the recombinant plasmid is pMY402 and the inducer is isopropyl-thiogalactoside (IPTG). The pMY402 recombinant plasmid is the pMMB66EH plasmid into which a 4.7 kb XhoI fragment encoding the PmKR1 toluene monooxygenase genes has been inserted. In another preferred embodiment of the present invention, the microorganism host cell is *E. coli* FM5, the recombinant plasmid is pKMY287 and the inducer is heat (42° C.). The pKMY287 recombinant plasmid is the pCFM1146 plasmid into which a 4.7 kb XhoI fragment encoding the PmKR1 toluene monooxygenase genes has been inserted. Under certain assay conditions, these resulting recombinant host cells express toluene monooxygenase enzyme activity at levels exceeding the activity of wildtype PmKR1 cells from which the toluene monooxygenase genes were isolated.

Other preferred embodiments of the present invention include the recombinant plasmids pKMY336 and pKMY340 in *E. coli* FM5 cells and a particularly preferred embodiment is plasmid pKMY342 in PpY2500 cells (PpY2511). These cells synthesized the highest levels of TMO enzyme observed for recombinant microorganisms described herein.

Under alternative assay conditions, the levels of TMO activity detected in the recombinant host cells equal but do not exceed the activity detected in wildtype PmKR1 cells. However, it is advantageous to use the recombinant host cells for certain microbial bioconversions. Advantages of using recombinant host cells with cloned TMO genes according to the present invention versus PmKR1 cells in these bioconversions include: (i) the ability to use innocuous inducers (e.g., IPTG, heat, salicylate) instead of toluene for TMO enzyme induction, and (ii) the ability to prevent further conversion of product by enzymes of subsequent steps in the TMO pathway that are present in PmKR1 but not in the recombinant host cells. Thus, it is particularly advantageous to use the cloned TMO gene cluster to generate recombinant plasmids and recombinant host cells for certain bioconversions according to the present invention because the need for toluene, which is volatile and toxic, is eliminated as inducer of TMO enzyme activity. For large-scale bioconversions using fermentors or otherwise, the disadvantages of toluene vapors in the bioconversion process are clearly evident. For safety reasons, some laboratories simply do not permit the use of toluene vapors in their fermentation processes. Additionally, it is particularly advantageous to use the isolated and cloned TMO gene cluster in bioconversions because it can be manipulated and introduced into certain host cells that will not further convert the desired product obtained in the bioconversion using the TMO genes. In contrast, since wildtype PmKR1 cells contain the genes for the entire TMO pathway and not just the TMO genes for the first step of the pathway, further conversion of the product of the first step monooxygenase reaction by the PmKR1 cells is likely.

The present invention is directed to the characterization and nucleotide sequence analysis of an isolated gene cluster of five TMO genes (tmoA, B, C. D. E), localized on the 4.7 kb XhoI fragment from PmKR1. The five-gene cluster, when expressed in *E. coli* gave significant TMO activity. Expression of this gene cluster carrying mutations in the individual genes demonstrated that each of the five genes is essential for TMO activity. The present invention is further directed to the characterization and nucleotide sequence analysis of a sixth TMO gene (tmoF), isolated on an ~1.3 kb HindIII-XmaI fragment downstream of the five essential TMO genes. The product of the tmoF gene is useful to enhance the activity of the products of the tmoABCDE genes. The gene cluster of six TMO genes is localized on an ~6.7 kb HindIII-BamHI fragment or an ~4.7 kb HindIII-XmaI fragment isolated from PmKR1. Expression of the six-gene cluster gave significantly higher TMO enzyme activity than expression of the five-gene cluster.

The present invention is directed to certain microbial bioconversions using PmKR1 or the transformed microorganism host cells containing the PmKR1 toluene monooxygenase genes, in particular, the conversion of a selected phenyl compound to a selected phenolic compound. In a particularly preferred embodiment of the present invention, a method is provided for making p-hydroxyphenylacetic acid using the transformed microorganism host cells containing the PmKR1 toluene monooxygenase genes. The p-hydroxyphenylacetic acid is a valuable chemical intermediate in the preparation of certain antibiotics and certain β-adrenergic blocking agents. The present invention is also directed to a method for the microbial production of indigo from indole using PmKR1 cells or the transformed microorganism host cells containing the PmKR1 toluene monooxygenase genes.

The present invention is also directed to an improved method for the degradative bioconversion of trichloroethylene using transformed microorganism host cells containing the PmKR1 tmoABCDEF gene cluster. Further aspects and advantages of the present invention will become apparent to those skilled in the art upon consideration of the following detailed description.

BRIEF DESCRIPTION OF THE DRAWINGS

FIG. 5 shows the nucleotide sequence of an ~4.7 kb PmKR1 DNA region carrying the tmoABCDEF genes. A region of dyad symmetry is underlined.

FIG. 6 shows the sequence homology of the TmoC protein with the ferredoxin (NahA$_b$) of naphthalene dioxygenase and the ferredoxin (BdoB) of benzene dioxygenase. Vertical lines indicate identical amino acid residues. Double dots indicate evolutionarily related amino acid residues based on the Gap program in UWGCG software (Devereux et al., *Nucleic Acids Res.* 12: 387-395 (1984)) with the similarity threshold set at 0.5. The amino acid sequences of the TmoC protein and the naphthalene dioxygenase ferredoxin protein are deduced from nucleotide sequences of the tmoC gene and the NahA$_b$ gene of the NAH7 plasmid (see Yen and Serdar, supra), respectively. The amino acid sequence of the benzene dioxygenase ferredoxin protein was determined by Morrice et al., *FEBS Lett.* 231: 336-340 (1988) from the protein B of *P. putida* ML2 (NCIB 12190). A methionine residue is inserted at the N-terminus of this protein to reflect the nucleotide sequence.

DETAILED DESCRIPTION

Figure 1:
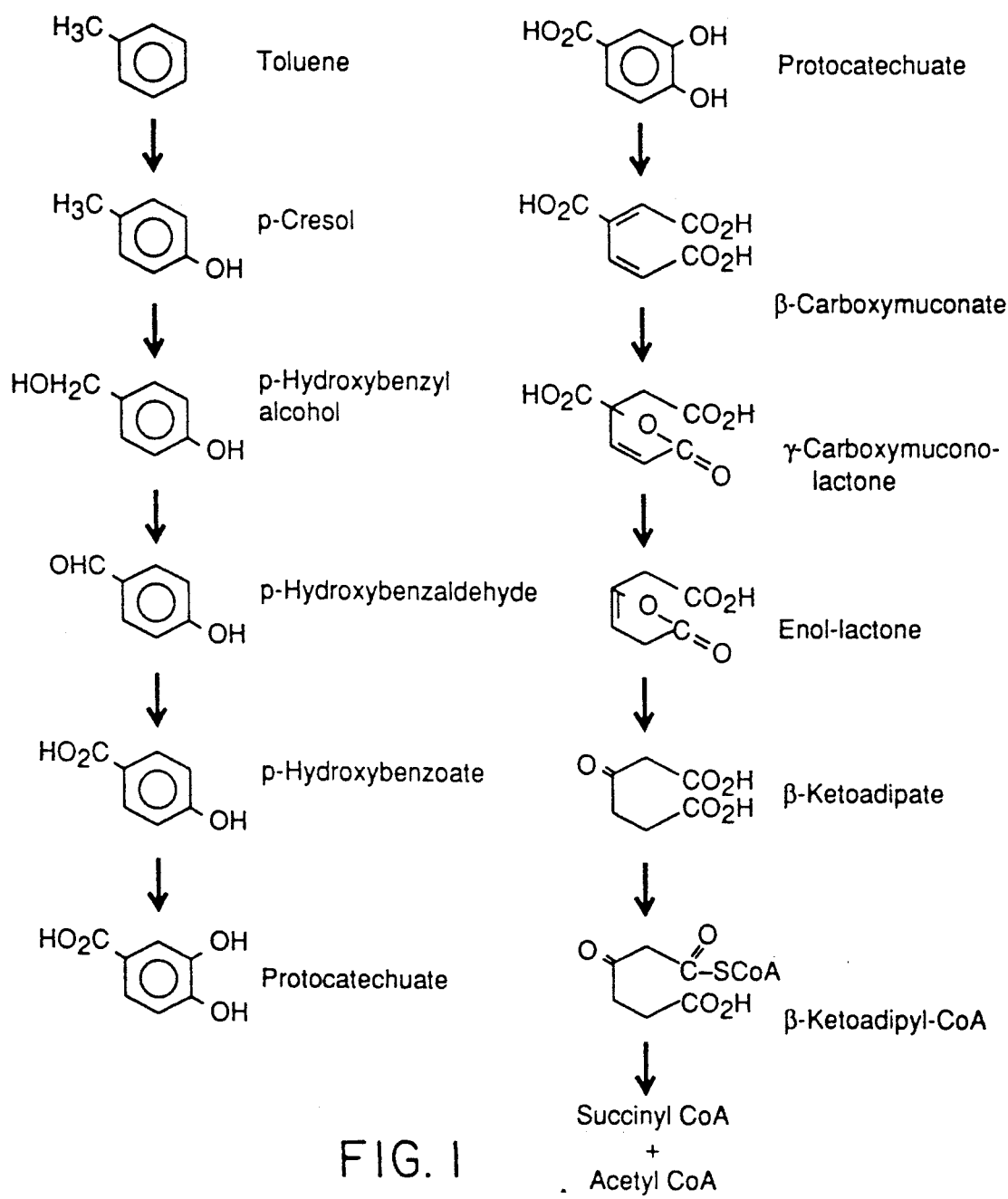
FIG. 1 illustrates the steps of the PmKR1 toluene monooxygenase (TMO) pathway.

The methods and materials that provide an illustration of the practice of the invention and that comprise the presently preferred embodiments relate specifically to plasmid-borne DNA gene segments of PmKR1 origin encoding the genes for the toluene monooxygenase enzyme system. After cloning into a plasmid, these plasmid-borne DNA gene segments can be introduced and expressed in certain microorganism host cells, for example, by conjugation or transformation.

Microorganism host cells containing PmKR1 toluene monooxygenase genes are useful in certain bioconversions. For example, many phenyl compounds, including toluene, methylphenylacetic acid, ethylphenylacetic acid, acetanilide, 2-phenylethanol, fluorobenzene and ethylbenzene may serve as substrates and be converted to phenolic compounds by the TMO system as described herein. In addition, the broad substrate specificity of the TMO system makes it potentially useful in biodegradation of toxic compounds. Methods for the complete degradation of trichloroethylene (TCE) by the TMO system have been described in co-pending and co-assigned U.S. patent application Ser. No. 177,640, filed Aug. 26, 1988, and hereby incorporated by reference in its entirety, and by Winter et al., *Bio/Technology* 7: 282-285 (1989). Improved methods for the complete degradation of TCE utilizing an isolated tmoABCDEF gene complex are described herein.

The 4.7 kb XhoI fragment identified from PmKR1 that encodes TMO protein components has now been further characterized. This XHoI fragment originally designated as 4.6 kb by restriction enzyme analysis was determined by DNA sequence analysis to be 4.7 kb. Five TMO genes (tmoABCDE) have been identified within this region by DNA sequencing analysis and N-terminal amino acid determination. Expression of this five-gene cluster carrying mutations in the individual genes demonstrated that each of the five genes is essential for TMO activity. A sixth gene, tmoF, was isolated on an ~1.3 kb HinDdIII-XmaI fragment downstream of the five essential TMO genes. The sixth gene, tmoF, is useful along with the tmoABCDE genes to yield enhanced TMO activity upon expression. The gene cluster of six TMO genes are localized on an ~6.7 kb HindIII-BamHI fragment or an ~4.7 kb HindIII-XmaI fragment from PmKRI. Expression of the six-gene cluster gave significantly higher TMO enzyme activity than expression of the five-gene cluster.

The potential exists, using recombinant DNA technology, to prepare variants, mutants or derivatives of one or more of the six TMO genes, which would encode a variant, mutant or derivative TMO protein. The complete gene sequence for each of the six TMO genes is disclosed in FIG. 5. Various modifications might result in single or multiple amino acid deletions, substitutions, insertions or inversions, for example, by means of in vitro mutagenesis of the underlying DNA by methods well-known in the art. In addition, various fragments of one or more of the proteins encode by the TMO genes, whether produced in vivo or in vitro, may possess the requisite useful TMO activity. Experiments have shown, for example, that changes in the N-terminal sequences of TmoF do not substantially change its functional activity. All such variations, modifications or fragments resulting in a variant, mutant or derivative of one or more of the six TMO genes are included within the scope of this invention so long as they encode the functional segment(s) of TMO protein(s) and the characteristic functional TMO activity remains substantially the same, e.g. unaffected in kind. Functional TMO activity results from a functional five-gene or six-gene TMO gene complex, as measured by the assays described herein, for example, in Example 11. From the disclosure of the TMO DNA sequences herein and the amino acid sequence of each of the six TMO genes, a TMO variant, mutant or derivative may be prepared and identified by those skilled in the art.

The invention is now illustrated by the following Examples, with reference to the accompanying drawings. Plasmids previously designated with the prefix "pKY" have been redesignated herein as "pKMY". The examples do not include detailed descriptions for conventional methods employed in the isolation of DNA, the cleavage of DNA with restriction enzymes, the construction of vectors, the insertion of DNA gene segments encoding polypeptides of interest into such vectors (e.g. plasmids) or the introduction of the resulting recombinant plasmids into microorganism host cells. Such methods are well-known to those skilled in the art of genetic engineering and are described in numerous publications including the following laboratory manuals: Maniatis et al., *Molecular Cloning—A Laboratory Manual*, Cold Spring Harbor Laboratory (1982); Davis et al., *Basic Methods in Molecular Biology*, Elsevier Science Publishing Co. (1986); *Current Protocols in Molecular Biology*, edited by Ausubel et al., Greene Publishing Associates and Wiley Interscience (1987); Sambrook et al., *Molecular Cloning: A Laboratory Manual* (Second Edition), Cold Spring Harbor Laboratory Press (1989). In addition to using published methods, methods for enzymatic cleavage, modification, and ligation of DNA may be achieved according to manufacturer's instructions distributed by various commercial suppliers of restriction enzymes, including New England Biolabs, Inc. (NEB), Beverly, MA 01915 and Boehringer Mannheim Biochemicals, Indianapolis, IN 46250.

EXAMPLE 1

Growth of PmKR1 Cells

*Pseudomonas mendocina* KR-1 was grown overnight at 30° in PAS medium or on a PAS agar plate (Chakrabarty, et al., *Proc. Natl. Acad. Sci. U.S.A.*. 70:1137–1140 1973) with toluene (supplied as vapor) for growth and for induction of the toluene monooxygenase genes.

EXAMPLE 2

Construction of PmKR1 BglII Library in *E. coli* HB101

A. Preparation of PmKR1 DNA

Total DNA was isolated from PmKR1 by conventional methods. Briefly, PmKR1 was inoculated into PAS medium containing toluene according to Example 1 and incubated with shaking at 30° C. overnight (13–17 hours). After incubation, PmKR1 cells in the stationary growth phase were collected by centrifugation. The cells were lysed and total PmKR1 DNA was then extracted and purified as described by Dhaese et al., *Nucleic Acid Res.* 7: 1837–1849 (1979).

B. Preparation of Plasmid DNA

Plasmid DNA may be isolated according to the method of Johnston and Gunsalus, *Biochem. Biophys. Res. Comm.* 75: 13–19 (1977). *E. coli* HB101 containing the pRK290 plasmid (Ditta, et al., *Proc. Natl. Acad Sci. U.S.A.* 77: 7347–7351 (1980)) was inoculated into L broth and incubated with shaking at 37° C. overnight. The bacterial cells were collected by centrifugation, lysed and the bulk of chromosomal DNA and cellular debris was removed by centrifugation. The pRK290 plasmid DNA was then purified by conventional techniques using cesium chloride/ethidium bromide density gradients.

c. Preparation of Recombinant Plasmid

Total PmKR1 DNA obtained in Part A above and pRK290 plasmid DNA obtained in Part B above were separately treated with the restriction endonuclease BglII, under conditions of complete digestion. The BglII digested PmKR1 DNA was mixed with BglII digested pRK290 plasmid DNA and the mixture then incubated with DNA ligase.

D. Transformation with Recombinant Plasmid

Transformation of *E. coli* with plasmid DNA may be achieved by the calcium chloride procedure originally described by Mandel and Higa, *J. Mol. Biol.* 53 159–162 (1970). The ligated DNA obtained in Part C above was used to transform *E. coli* HB101 and the transformed cells were plated on selection plates of L-agar containing 10 μg/ml tetracycline. Only those cells which are successfully transformed and which contain the pRK290 plasmid or a recombinant pRK290 plasmid with PmKR1 DNA can grow on the selection plates. Colonies which grew on the selection plates were tested for the presence of recombinant plasmids containing PmKR1 toluene monooxygenase genes by the conjugation and complementation screening assay of Example 3.

EXAMPLE 3

Conjugation and Complementation Screening Assay

A complementation assay involving plasmid transfer via bacterial conjugation was used to screen the PmKR1 BglII library made according to Example 2 and the PmKR1 SacI library made according to Example 8 in order to detect recombinant plasmids containing PmKR1 toluene monooxygenase genes. Accordingly, plasmids were transferred between bacterial strains by the conjugation ("mating") procedure (spot crosses) described by Yen and Gunsalus, *Proc. Natl. Acad. Sci. U.S.A.*, 79:874–878 (1982). This procedure is summarized briefly as follows.

Colonies were removed from the selection plates of Example 2 or Example 8 by gentle scraping in L-broth with a slide. The resulting bacterial cell suspension was washed to remove any tetracycline and suspended in L-broth for the mating. Suspensions of donor cells, helper cells (if necessary) and recipient cells in logarithmic phase were mixed in equal volumes. Small aliquots of the mixture were placed on L-agar plates thus allowing all cell types to grow. After overnight incubation at 30° C., the cells were replated on a PAS agar selection plate containing 50 μg/ml tetracycline. Toluene was provided as sole carbon source for growth. Toluene vapor was supplied to the selection plate by taping a cotton-stoppered toluene containing tube to the lid of the plate. This selection plate permits only the desired trans-conjugates to grow. In all experiments performed, the donor cells were from an *E. coli* HB101 library (either the BglII library of Example 2 or the SacI library of Example 8) carrying a recombinant plasmid (pRK290 in Example 2 or pKMY235 in Example 8 containing PmKR1 gene segments) to be transferred in the mating. The helper cells used were *E. coli* HB101 cells carrying the helper plasmid pRK2013 which provided the transferring functions for those transferring plasmids which do not carry the tra genes. Alternatively, the helper plasmid pRK2013 was introduced directly into the donor cells to provide its transferring function. The recipient strain was one of several mutant strains of *Pseudomonas mendocina KR*-1 (Pm Y4001, Pm Y4002, Pm Y4007) prepared as described in Example 4. Each of the mutant strains has a defective toluene monooxygenase gene and is unable to convert toluene to p-cresol. When a recombinant plasmid containing the specific PmKR1 toluene monooxygenase gene which is defective in the recipient strain has been successfully transferred during conjugation, the resulting transconjugate will be able to grow as a colony on the selection plates containing toluene as the sole carbon source for growth.

The colonies which grew on the selection plates were purified by restreaking each colony once or twice on a selection plate. These transconjugates are further manipulated according to Example 5.

EXAMPLE 4

Preparation of *Pseudomonas mendocina* KR-1 Mutant Strains

PmKR1 cells were mutagenized and the toluene monooxygenase defective mutants were isolated according to the following protocol. Cells were grown in 5 ml of L broth to O.D.$_{660}$ of approximately 0.7 and resuspended into 2 ml of 50 mM citrate buffer pH 6.0 containing N-methyl-N'-nitro-N-nitrosoguanidine (nitrosoguanidine) at a concentration of 0.1 mg per ml. After incubation at room temperature for 20 minutes, the cells were washed twice with 2 ml of 1 M phosphate buffer pH 7.0 and resuspended into 50 ml of L broth. After growth overnight, the cells were streaked on L agar plates for single colonies. The individual colonies were picked and streaked onto PAS plates containing toluene or p-cresol (2.5 mM) as sole carbon source. The toluene monooxygenase defective mutants, PmY4001, PmY4002 and PmY4007 were isolated as strains which grew on p-cresol but not on toluene. The toluene monooxygenase assay as described in Example 11 further confirmed that these mutants have a defective toluene monooxygenase enzyme system.

Similar mutagenesis techniques may be used to obtain mutants defective in the enzyme p-cresol hydroxylase or p-hydroxybenzaldehyde dehydrogenase of the TMO pathway. After nitrosoguanidine treatment of PmKR1 cells as described above, p-cresol hydroxylase defective mutants can be isolated as strains which grow on p-hydroxybenzyl alcohol but not on p-cresol and p-hydroxybenzaldehyde dehydrogenase defective mutants can be isolated as strains which grow on p-hydroxybenzoate but not p-hydroxybenzylalcohol or p-hydroxybenzaldehyde.

EXAMPLE 5

Isolation of 9.4 kb BglIII Fragment

A number (12) of the transconjugate colonies of PmY4001 containing PmKR1 toluene monooxygenase genes isolated according to Example 3 were further characterized as follows. Each colony was grown and plasmid DNA was isolated by conventional methods. The plasmid DNA from each isolate was used to transform *E. coli* HB101 cells. The plasmid in each transformant was transferred to PmY4001 by conjugation according to Example 3 except that the selection plates contained tetracycline and glucose (2 mg/ml). Each transconjugate was tested for growth on toluene by plating the cells on PAS agar supplemented with 50 μg/ml tetracycline and toluene vapor. After the toluene monooxygenase complementing activity of the plasmid was confirmed in the transconjugates each such HB101 transformant was grown and plasmid DNA was isolated by conventional methods.

The DNA was digested with BglII and a 9.4 kb fragment was isolated from each transconjugate colony which complemented each PmKR1 mutant strain of Example 4 for toluene utilization. This result indicated that the 9.4 kb BglIII fragment from PmKR1 contained one or more toluene monooxygenase genes. Two SacI sites were mapped close to one end of the 9.4 kb BglII fragment. No TMO activity could be detected from the pRK290 plasmid (Example 2) carrying this 9.4 kb BglII insert in either *E. coli* HB101 or *P. putida* KT2440 (Bagdasarian et al., Gene 16: 237-247 (1981)). Subcloning of this insert into *E. coli* expression vectors pUC18 and pUC19 (Yanisch-Perron et al., Gene 33 103-119 (1985)) did not lead to the detection of any TMO activity. Thus, the 9.4 kb BglIII fragment did not appear to contain the entire TMO gene cluster required for activity.

EXAMPLE 6

Construction of pKMY235 Plasmid Vector

Figure 2:
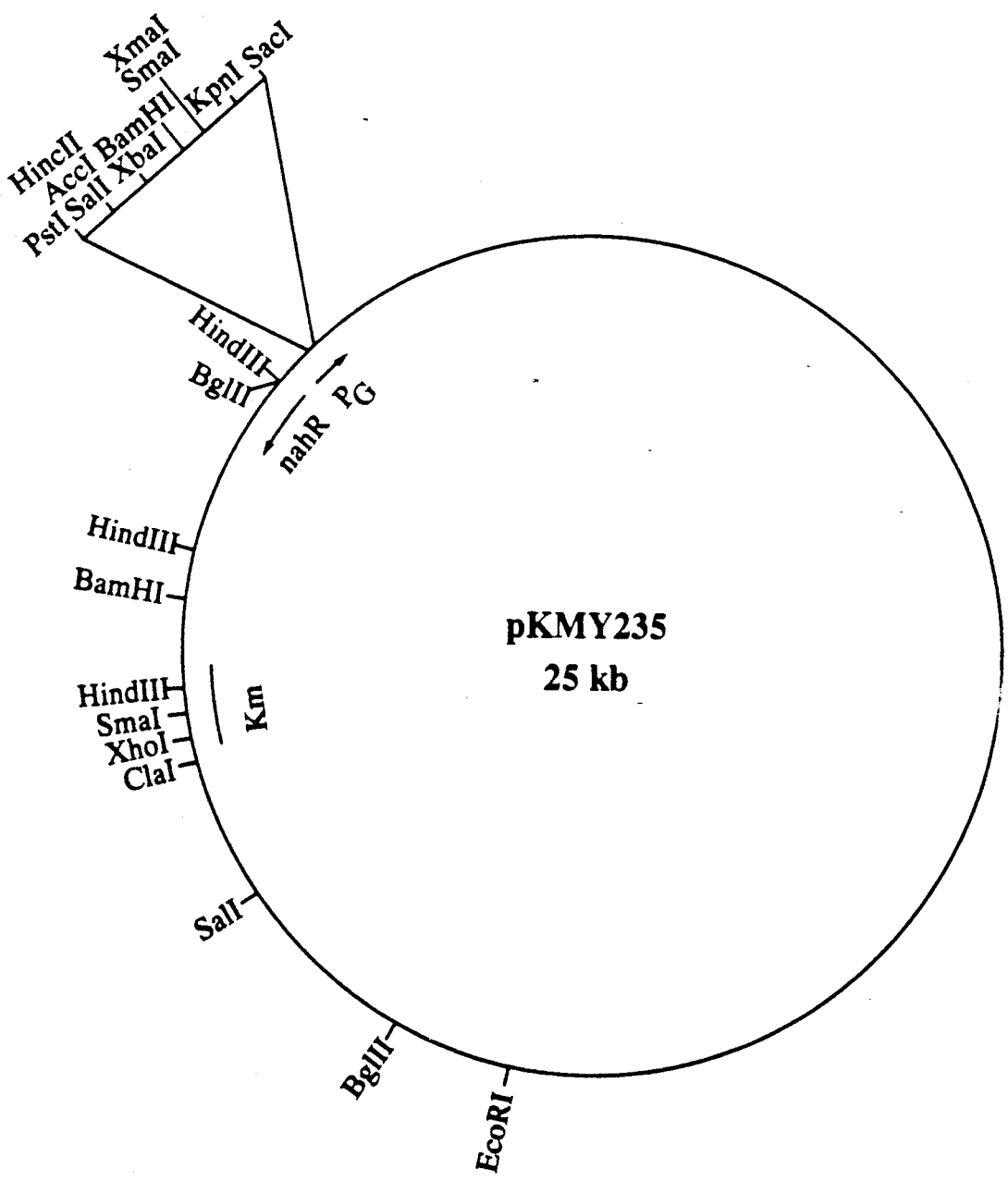
FIG. 2 shows a map of the pKMY235 plasmid vector.

The starting material for the construction of the pKMY235 plasmid was the pKY217 plasmid described by Yen and Gunsalus, *J. Bacteriol* 162: 1008-13 (1985). The pKMY235 plasmid was constructed according to the following series of steps. In the first step, two adjoining HindIII fragments (~1.1 and ~3.2 kb) from pKY217 containing the nahR and nahG genes was cloned into the HindIII site of the pKT240 plasmid described by Bagdasarian et al., Gene 26: 273-82 (1983). The resulting plasmid from this first step was designated pKMY219. In the second step, an ~7 kb BamHI -SacI fragment from pKMY219 containing the nahR and nahG genes was cloned into the BamHI and SacI sites of the pKT231 plasmid described by Bagdasarian et al. Gene 16: 237-47 (1981). The resulting plasmid was designated pKMY223. In the next step, an ~6 kb PstI fragment from pKMY223 containing the nahR gene, ~200 base pairs of the nahG gene and the pKT231 gene conferring kanamycin resistance was cloned into the PstI site of the pUC19 plasmid described by Yanisch-Perron et al., Gene 103-119 (1985). The resulting plasmid was designated pKMY256. The orientation of the ~6 kb PstI fragment in pKMY256 placed the multicloning site of pUC19 from the SalI to the EcoRI site immediately downstream to the PstI site in the nahG gene. In the final step, an ~5.4 kb BstEII-EcoRI fragment from pKMY256 containing the gene conferring kanamycin resistance, the nahR gene, ~200 base pairs of the nahG gene and a multiple cloning site was end-filled with the large fragment of *E. coli* DNA polymerase I and inserted into the pRK290 plasmid described by Ditta et al., *Proc. Natl. Acad. Sci. U.S.A.* 77; 7347-7351 (1980) to replace the ~1 kb SmaI fragment of pRK290. The resulting plasmid was designated pKMY235 and a map of pKMY235 is shown in FIG. 2.

EXAMPLE 7

Construction of pcFM1146 Plasmid Vector

The plasmid pCFM1146 is an *E. coli* cloning vector similar to PCFM4722 (Burnette et al., *Bio/Technology* 6: 699-706.1988)). The starting material for the construction of the pCFM1146 plasmid was the pCFM836 plasmid. A detailed description of the construction of expression vectors, including pCFM836, is described in U.S. Pat. No. 4,710,473, which is hereby incorporated by reference in its entirety. The pCFM836 plasmid contains a heat inducible promoter, a restriction site bank (cloning cluster), plasmid origin of replication, a transcription terminator, genes regulating plasmid copy number, and a gene conferring kanamycin resistance but no synthetic ribosome binding site immediately preceding the cloning cluster. The pCFM1146 plasmid (A.T.C.C. accession no. 67671) was derived from pCFM836 by substituting the small DNA sequence between the unique ClaI and XbaI restriction sites with the following oligonucleotide

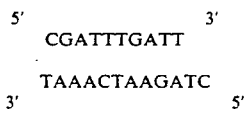

and by destroying the two endogenous NdeI restriction sites by cleavage with NdeI and then end-filling with T4 polymerase enzyme, followed by blunt end ligation.

EXAMPLE 8

Construction of PmKR1 SacI Library in *E. coli* HB101

The pKMY235 plasmid vector prepared according to Example 6 was used to construct a SacI library in *E. coli* HB101 according to conventional techniques for constructing genomic libraries. Total DNA from PmKR1 was isolated as described in Example 2, Part A. The isolated PmKR1 DNA was treated with the restriction endonuclease SacI under conditions of partial digestion. In order to produce a population of DNA fragments enriched in those fragments containing some or all of the PmKR1 toluene monooxygenase genes for use in constructing this SacI library, the partially digested PmKR1 DNA was fractionated by size using a 10%-40% sucrose density gradient according to conventional procedures. After centrifugation for 24 hours at 26,000 rpm in an SW-28 rotor, the DNA fractions were collected and tested by hybridization. The 9.4 kb BglII fragment isolated from the BglII library constructed according to Example 3, is known to complement each PmKR1 mutant strain for toluene utilization according to Example 5 and thus is likely to contain at least one of the PmKR1 toluene monooxygenase genes. The plasmid pUC19 carrying the 9.4 kb fragment was radiolabeled and used as a probe to select hybridizing fractions from the sucrose gradient. The hybridizing fractions were pooled to provide a population of DNA fragments enriched in PmKR1 toluene monooxygenase genes. This enriched population of DNA fragments was used to construct the SacI library in *E. coli* HB101. They were randomly cloned into the SacI site of plasmid pKMY235 as follows.

The enriched SacI digested PmKR1 DNA was mixed with SacI digested pKMY235 plasmid DNA and incubated with DNA ligase. The ligated DNA was used to transform *E. coli* HB101 and the transformed cells were plated onto selection plates of L-agar containing 10 μg/ml tetracycline. Only those cells which were successfully transformed and containing the pKMY235 plasmid or a recombinant pKMY235 plasmid with PmKR1 DNA can grow on the selection plates. Transformed colonies were tested for PmKR1 toluene monooxygenase genes by the conjugation and complementation assay of Example 3.

EXAMPLE 9

Isolation of 20.4 kb SacI Fragment

A number (10) of the transconjugates which utilized toluene as a sole carbon source were further characterized by isolating the plasmid DNA, transforming *E. coli* HB101, and conjugating into PmY4001 to test for growth on toluene according to Example 5. An *E. coli* HB101 transformant containing a recombinant pKMY235 plasmid (designated pKMY266, A.T.C.C. accession no. 67672) carrying toluene monooxygenase genes was grown and plasmid DNA was isolated by conventional methods. Restriction enzyme analysis of the insert in pKMY266 plasmid indicated that it carried two 10.2 kb SacI fragments (previously designated two SacI fragments of 10.2 kb and 10.3 kb, respectively). One of the 10.2 kb SacI fragments contains ~8 kb of the ~9.4 kb BglII fragment described in Example 5.

Plasmid pKMY266 containing the ~20.4 kb (previously designated 20.5 kb) SacI insert described above, allowed the utilization of toluene by PmY4001. Despite the complementation pattern, no TMO enzyme activity (according to the alternative method of Example 11) could be detected in *E. coli* HB101 carrying pKMY266. Since the insert in pKMY266 consisted of two different SacI fragments of identical size, each was subcloned and expressed in the high-copy-number *e. coli* expression vector pUC19 described by Yanisch-Perron et al., *Gene* 103-119 (1985). This experiment led to the successful mapping of the TMO genes as described in Example 10 below.

EXAMPLE 10

Construction of Recombinant Plasmids to Map the Toluene Monooxygenase Genes

This example presents results on the mapping of the TMO genes and determination of TMO activities in various recombinant strains based on earlier constructs and TMO assay procedure (Example 11, Part A). Further mapping of the TMO genes and determination of TMO activities in more recently constructed strains based on the alternative TMO assay procedure described in Example 11, Part B is presented in Example 16.

One of the SacI fragments described in Example 9, when cloned into pUC19 (pKMY277) and expressed in *E. coli* JM109, led to the synthesis of a blue pigment which was chloroform soluble and water insoluble. Production of the blue pigment was also observed from P. putida cells harboring pKMY266 and was dependent on the presence of indole. This blue pigment was identified as indigo. A low level of TMO enzyme activity was detected from the *E. coli* JM109 carrying pKMY277 (Table I). Further mapping of the toluene monooxygenase genes correlated the indigo-producing property with the presence of toluene monooxygenase activity. (See Table I in Example 11 and also Table III in Example 16).

Figure 3:
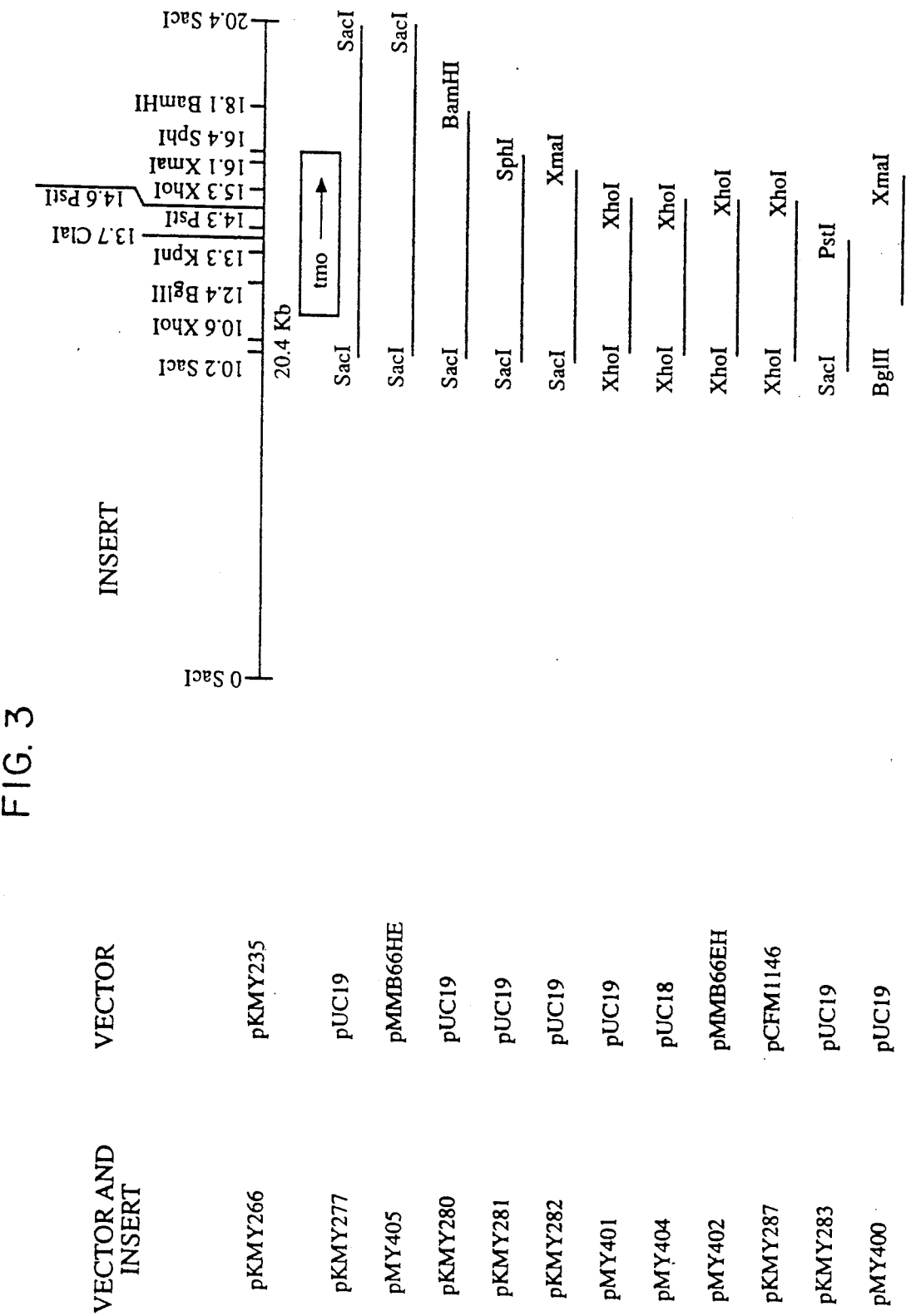
FIG. 3 illustrates a summary of recombinant plasmids, plasmid vectors and restriction maps of the PmKR1 DNA segments containing toluene monooxygenase genes.

The ~10.2 kb SacI fragment of pKMY277 was digested with a series of restriction enzymes and a partial restriction map was generated as shown in FIG. 3. Based on this restriction map, a series of DNA fragments were deleted from one end of the 10.2 kb SacI fragment in pKMY277 to generate plasmids pKMY280, pKMY281, pKMY282 and pKMY283 shown in FIG. 3. An ~4.7 kb XhoI fragment of pKMY282 was subcloned into the SalI site of pUC19 to generate the plasmid pMY401. An ~4.6 kb BamHI-SphI fragment of pMY401 was inserted into the *E. coli* expression vector pUC18 described by Yanisch-Perron et al., *Gene* 33: 103-119 (1985) to generate the plasmid pMY404. The pUC18 plasmid is identical to pUC19 except the polycloning site is in an opposite orientation with respect to the lac promoter. As a result, the ~4.7 XhoI fragment was inserted into the pUC18 plasmid in an opposite orientation to that in the pUC19 plasmid with respect to the lac promoter. The ~4.7 kb XhoI fragment of pKMY277 was also cloned into the broad host range plasmid vector pMMB66EH described by Furste et al., *Gene* 48: 119-131 (1986) to construct the plasmid pMY402. In addition, as shown in FIG. 3, an ~2.2 kb SacI-BglII fragment was deleted from the left end of the ~5.9 kb SacI-XmaI fragment of pKMY282 by digesting pKMY282 DNA with SacI and BglII, filling the ends with the large fragment of *E. coli* DNA polymerase I and ligating the ends. The resulting plasmid was designated pMY400.

As shown in Table I (according to the assay of Example 11), pMY402 containing cells responded to IPTG for induction of the toluene monooxygenase genes. This result located the toluene monooxygenase genes in the ~4.7 kb XhoI fragment and revealed the direction of transcription of the toluene monooxygenase genes as from left to right shown in FIG. 3. The difference in the orientation of the ~4.7 kb XHoI fragment in pMY401 and pMY404 as well as the difference in toluene monooxygenase activity in pMY401 and pMY404 containing cells (Table I) are also consistent with this transcriptional direction of the toluene monooxygenase genes. In order to express the toluene monooxygenase genes at a high level, the ~4.7 kb XhoI fragment of pKMY282 was also cloned into the XhoI site of the *E. coli* expression vector pCFM1146 (as described in Example 7) to construct pKMY287.

EXAMPLE 11

Toluene Monooxygenase Assays

A. Conditions for Assay

Cells were grown in PAS medium containing 0.4% glutamate or in L broth to saturation. They were resuspended into an appropriate volume of the same medium to an O.D.$_{660}$ of 3.0. An aliquot of the cells was used for the determination of protein concentration by the method of Bradford, *Anal. Biochem.* 72: 248 (1976) using the Bio. Rad Protein Assay. An aliquot of 0.5 ml of cells was mixed with 4 μmoles of p-cresol in 10 μl and 15 nmole of radioactive toluene (toluene ring-$^{14}$C, Sigma Chemical Co., 56.3 mCi/mmole) in 5 μl and the mixture was incubated at room temperature with occasional vortexing for 20 minutes. After incubation, 20 μl of the mixture were spotted on a small piece of a thin-layer chromatography plate and the plate was air-dried for twenty minutes. The nonvolatile radioactivity remained on the filter was determined in a liquid scintillation counter and was used to calculate the amount of toluene degradation product on the plate and the specific activity of toluene monooxygenase. The results are presented in Table I.

B. Conditions for Alternative Assay

Alternatively, toluene monooxygenase activity could be assayed by a procedure similar to the assay described for naphthalene dioxygenase by Ensley et al., in *Microbial Metabolism and the Carbon Cycle* (Hagedorn et al., eds.), Harvard Academic Publishers, New York (1988) at p. 437. Late log-phase cells were diluted into L-broth to a density of O.D.$_{550}$=0.5 for the assay. The reactions were initiated by adding 15 nmoles of $^{14}$C-toluene (Sigma, 40.60 mCi/mmol) to 0.5 ml of cells in L-broth. After incubation at room temperature for 5 minutes, aliquots of 20 μl were spotted on small strips of thin-layer chromatography plate. The plates were air-dried for 20 minutes and counted in a scintillation counter to determine the remaining radioactivity. Specific activity of TMO was expressed as nmoles of nonvolatile material produced from $^{14}$C-toluene per minute per milligram of whole cell protein. The protein concentration was determined by the method of Bradford, *Anal. Biochem.* 72: 248, using the Bio-Rad protein assay kit obtained from Bio-Rad Laboratories, Richmond, CA 94804. For the protein determination, cells were resuspended in 0.1 N NaOH and incubated in a boiling water bath for 20 minutes, then assayed with the kit. The results of this alternative TMO assay are presented in Table III, Example 16.

TABLE I

Expression of the Toluene Monooxygenase (TMO) genes in *E. coli* and *P. mendocina*

| Plasmid | Inducer | Host cell | Specific Activity of TMO (nmole min$^{-1}$mg$^{-1}$) | Indigo Formation |
|---|---|---|---|---|
| pAUT1 | Toluene | *P. mendocina* KR1 | 0.130 | + |
| pAUT1 | None | *P. mendocina* KR1 | 0.010 | + |
| pKMY266 | None | *P. putida* KT2440 | 0.020 | + |
| pKMY277 | None | *E. coli* JM109 | 0.010 | + |
| pMY405 | None | *E. coli* HB101 | 0.005 | − |
| pMY405 | IPTG | *E. coli* HB101 | 0.015 | + |
| pKMY280 | None | *E. coli* JM109 | 0.010 | + |
| pKMY281 | None | *E. coli* JM109 | 0.010 | + |
| pKMY282 | None | *E. coli* JM109 | 0.010 | + |
| pKMY283 | None | *E. coli* JM109 | 0.005 | − |
| pMY400 | None | *E. coli* JM83 | 0.005 | − |

TABLE I-continued

Expression of the Toluene Monooxygenase (TMO) genes in *E. coli* and *P. mendocina*

| Plasmid | Inducer | Host cell | Specific Activity of TMO (nmole min$^{-1}$mg$^{-1}$) | Indigo Formation |
|---|---|---|---|---|
| pMY401 | None | *E. coli* JM83 | 0.035 | + |
| pMY404 | None | *E. coli* JM83 | 0.010 | + |
| pMY402 | None | *E. coli* HB101 | 0.005 | − |
| PMY402 | IPTG | *E. coli* HB101 | 0.200 | + |
| pKMY287 | Heat | *E. coli* FM5 | 0.500 | + |
| pUC19 | None | *E. coli* JM109 | 0.005 | − |
| pMMB66EH | IPTG | *E. coli* HB101 | 0.005 | − |
| pCFM1146 | Heat | *E. coli* FM5 | 0.005 | − |

EXAMPLE 12

Conversion of Certain Phenyl compounds to Certain Phenolic compounds

A. Conversion by PmKR1 Cells

Many phenyl compounds, including toluene, methylphenylacetic acid, ethylphenylacetic acid, 2-phenylethanol, acetanilide, fluorobenzene and ethylbenzene, may serve as substrates and thus be converted to phenolic compounds via para-hydroxylation by the toluene monooxygenase system of PmKR1. The following schemes illustrate several possible conversions:

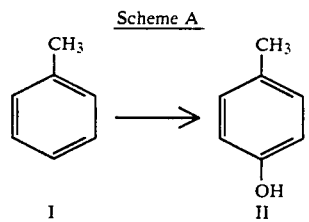

wherein:
I is toluene
II is p-cresol

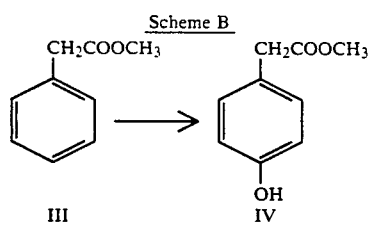

wherein:
III is methylphenylacetic acid
IV is p-hydroxymethylphenylacetic acid

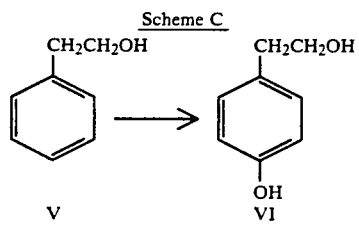

wherein:
V is 2-phenylethanol

VI is p-hydroxy-2-phenylethanol

For each conversion, a phenyl compound substrate (for example, Formulas, I, III, or V) was mixed with PmKR1 cells, incubated for a period sufficient to effect the bioconversion and then assayed for the presence of phenolic compounds as follows.

*Pseudomonas mendocina* KR1 cells were grown at 25° C.-30° C. in 50 ml PAS medium supplemented with 0.4% glutamate to stationary phase (12–16 hours) in the presence (induced) or absence (uninduced) of toluene vapor supplied from 2.5 ml toluene. An aliquot of 5–50 ml cells were resuspended into the same volume of the same medium or concentrated 2.5 fold in the same medium. A given amount of the substrate equivalent to form a 15–30 mM solution was mixed with the cells and the mixture was incubated at 25° C.-30° C. with vigorous shaking for 1–24 hours. Typically the mixture was incubated for 5–6 hours. Formation of phenolic compounds was determined according the assay method of Gupta et al., *Clin. Biochem.* 16 (4): 220–221 (1983). The assay results for conversion of several phenyl substrates to phenolic compounds at various times and temperatures of incubation are shown in Table II.

TABLE II

Synthesis of Phenolic Compounds by Toluene Monooxygenase of *Pseudomonas mendocina* KR1

| Substrate (Time and Temperature of Incubation) | O.D.$_{660}$ reading in Assay |
|---|---|
| acetanilide (6 hrs., 25° C.) | 1.07 |
| fluorobenzene (24 hrs., 25° C.) | 0.73 |
| methylphenylacetate (6 hrs., 30° C.) | 0.23 |
| ethylphenylacetate (6 hrs., 30° C.) | 0.13 |
| ethylbenzene (6 hrs., 30° C.) | 0.37 |
| 2-phenylethanol (5 hrs., 30° C.) | 0.16 |
| substrate in uninduced culture | 0.03 |

B. Conversion by Microorganism Host Cells Containing Recombinant Plasmids encoding PmKR1 Toluene Monooxygenase Genes The same conversions according to Part A may be accomplished by using microorganism host cells containing the recombinant plasmids of Examples 10, 16, and 19. Any of the recombinant plasmids (except pKMY283 or pMY400) which encode functional -PmKR1 toluene monooxygenase genes as described in Example 10 may be used to transform an appropriate microorganism host cell. A preferred method is to use pMY402 as the recombinant plasmid, *E. coli* HB101 as the microorganism host cell and IPTG as the inducer, as described in Example 11. The resulting strain was designated EcY5072 (HB101 /pMY402). Another preferred method is to use pKMY287 or pKMY336 as the recombinant plasmid, *E. coli* FM5 as the microorganism host cell and heat (42° C. for 1.5 or 3 hrs.) as the inducer. The resulting strains were designated EcY5082 (FM5/pKMY287) and EcY5236 (FM5/pKMY336), respectively. A particularly preferred method is to use pKMY342 as the recombinant plasmid, PpY2500 as the microorganism host cell and sodium salicylate (0.35 mM in L-broth throughout cell growth) as the inducer. The resulting strain was designated PpY2511 (PpY2500/pKMY342).

For each conversion, a phenyl compound (for example, Formulas I, III or V) is mixed with EcY5072 (HB101/pMY402), EcY5082 (FM5/pKMY287), EcY5236 (FM5/pKMY336) or PpY2511 (PpY2500/pKMY342) cells. The mixture is incubated for a period sufficient to effect the bioconversion and then assayed as described in Part A for the presence of phenolic compounds. For each bioconversion with EcY5072 (HB101/pMY402) cells, the cells are grown and assayed in the presence of IPTG to induce PmKR1 toluene monooxygenase activity as follows. Cells are grown in PAS medium containing 0.4% glutamate and 1 mM IPTG or grown in L broth with 1 mM IPTG to saturation. The cells are resuspended in an appropriate volume of the same medium to an $O.D._{660}$ of 3.0 and incubated with substrate and assayed as described in Part A. For each bioconversion with EcY5082 (FM5/pKMY287) or EcY5236 (FM5/pKMY336) cells, the cells are grown under the following temperature conditions to induce PmKR1 toluene monooxygenase activity. EcY5082 (FM5/pKMY287) or EcY5236 (FM5/pKMY336) cells are grown in L broth to an $O.D._{660}$ of 0.4. The cultures are incubated with shaking at 42° C. for 3 hours and then shifted to 30° C. to incubate for another 2 hours. Cells are resuspended in fresh L broth to an $O.D._{660}$ of 3.0 and incubated with substrate and assayed as described in Part A. For indigo production (Example 15) using these two strains, the cells are incubated at 30° for 24 hours after induction at 42° C. For each bioconversion with the PpY2511 strain, the cells are grown and induced under the following conditions. The cells are grown in L broth to saturation in the presence of 0.35 mM sodium salicylate to induce toluene monooxygenase production. Cells are resuspended in the same medium to an $O.D._{660}$ of 3.0 and incubated with substrate and assayed as described in Part A.

EXAMPLE 13

Conversion of Toluene to p-Hydroxyphenylacetic Acid

A. Conversion by PmKR1 Cells

For the conversion of toluene substrate to p-hydroxyphenylacetic acid, toluene is mixed with a PmKR1 mutant containing defective p-hydroxybenzaldehyde dehydrogenase as described in Example 4 and incubated for a period sufficient to effect the conversion of toluene to p-hydroxybenzyl alcohol. In the second step, the cell mixture containing the p-hydroxybenzyl alcohol intermediate is reacted with nickel (Ni) and carbon monoxide (CO) in such concentrations and at such temperatures sufficient to convert the p-hydroxybenzyl alcohol to p-hydroxyphenylacetic acid, according to the methods of U.S. Pat. Nos. 4,482,497; 4,659,518; 4,631,348, which are hereby incorporated by reference. The conversion scheme is illustrated as follows:

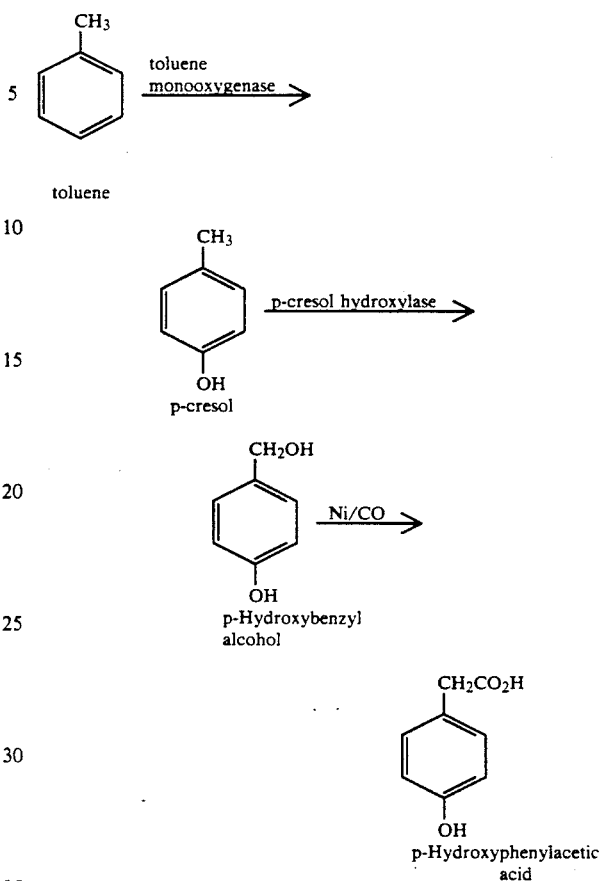

B. Conversion by Microorganism Host Cells Containing Recombinant Plasmids encoding PmKR1 Toluene Monooxygenase Genes The same conversion according to Part A may be accomplished by using microorganism host cells harboring recombinant plasmid(s) carrying the p-cresol hydroxylase gene and the TMO genes. The p-cresol hydroxylase genes may be isolated by cloning of restriction fragments from PMKR1 or plasmid pND50 (Hewetson et al., Genet. Res. Camb. 32: 249–255, 1978) which allow p-cresol hydroxylase defective mutants of PMKR1 (Example 4) to use p-cresol as a carbon and energy source. Alternatively, it may be isolated by using the sequence of TMO genes as a probe to clone overlapping restriction fragments that contain the gene. The possibility exists that the ~10.2 kb SacI fragment containing the TMO gene cluster (Example 10) contains the p-cresol hydroxylase genes. For use in the bioconversion described in Part A, the p-cresol hydroxylase genes may be cloned and expressed in plasmid pMY402, pKMY287, pKMY336 or pKMY342 (Examples 10, 16, and 19) each of which contains a functional TMO gene cluster. Alternatively, the p-cresol hydroxylase genes may be cloned and expressed in another plasmid which can be introduced into strains which contain plasmid pMY402, pKMY287, pKMY336 or pKMY342.

For the conversion as illustrated in Part A, toluene is mixed with induced cells containing the p-cresol hydroxylase genes and the TMO genes. The mixture is incubated for a period sufficient to effect the conversion of toluene to p-hydroxybenzyl alcohol, and then is reacted with Ni and CO according to Part A to effect the conversion to p-hydroxyphenylacetic acid.

EXAMPLE 14

Conversion of Methylphenylacetic Acid to p-Hydroxyphenylacetic Acid

A. Conversion by PMKR1 Cells

For the conversion of methylphenylacetic acid substrate to p-hydroxyphenylacetic acid, methylphenylacetic acid is mixed with PmKR1 grown as described in Example 12 and incubated for a period sufficient to effect the conversion of methylphenylacetic acid to p-hydroxymethylphenylacetic acid. In the second step, the cell mixture containing the p-hydroxyphenylacetic acid intermediate is subjected to acid hydrolysis at acid concentrations and temperatures sufficient to convert the p-hydroxymethylphenylacetic acid to p-hydroxyphenylacetic acid. The conversion scheme is illustrated as follows:

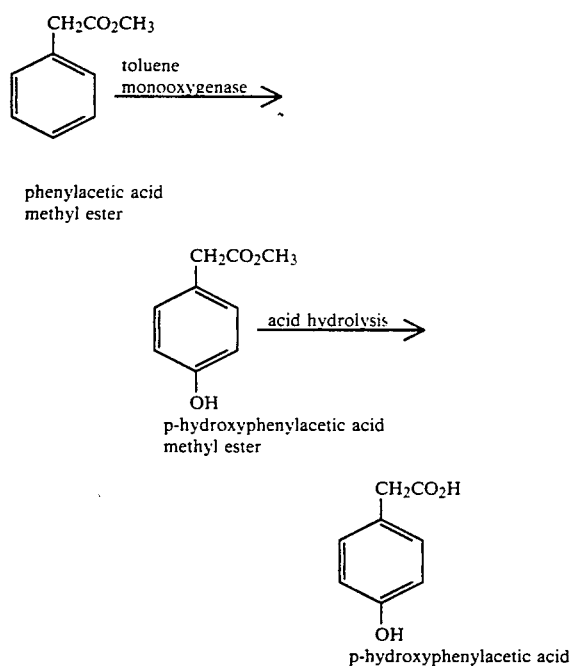

B. Conversion by Microorganism Host cells Containing Recombinant Plasmids encoding PmKR1 Toluene Monooxygenase Genes The same conversion according to Part A may be accomplished by using microorganism host cells containing the recombinant plasmids of Examples 10, 16, and 19 that carry a functional TMO gene cluster isolated from PmKR1. A preferred method is to use EcY5072 (HB101 /pMY402) cells. Another preferred method is to use EcY5082 (FM5/pKMY287) or EcY5236 (FM5/pKMY336) cells. A particularly preferred method is to use PpY2511 (PpY2500/pKMY342) cells.

For the conversion as illustrated in Part A, methylphenylacetic acid is mixed with: EcY5072 (HB101 /pMY402) cells grown and induced with IPTG, EcY5082 (FM5/pKMY287) or EcY5236 (FM5/pKMY336) cells grown and induced with heat, or, PpY2511 (PpY2500/pKMY342) cells grown and induced with sodium salicylate, as described in Example 12. The mixture is incubated for a period sufficient to effect the bioconversion of p-hydroxymethylacetic acid and then the mixture is subjected to acid hydrolysis at acid concentrations and temperatures sufficient to yield p-hydroxyphenylacetic acid.

EXAMPLE 15

Conversion of Indole to Indigo

A. Conversion by PMKR1 Cells

For the conversion of indole substrate to indigo, 50 μg/ml indole was mixed with PMKR1 cells grown as described in Example 12 and incubated for a period sufficient to effect the conversion of indole to indigo, generally 48 hours. The indigo may be isolated from the cell mixture by the procedure described by Ensley in Example 5 of U.S. Pat. No. 4,520,103.

B. Conversion by Microorganism Host cells Containing Recombinant Plasmids encoding PmKR1 Toluene Monooxygenase Genes The same conversion according to Part A may be accomplished by using microorganism host cells containing the recombinant plasmids of Examples 10 and 16 that carry a functional TMO gene cluster isolated from PmKR1. A preferred host strain is one that produces indole endogenously in the presence of an inexpensive carbon source, such as glucose. An example of such a host is E. coli or a particular strain of E. coli with an enhanced rate of indole synthesis. A preferred method is to use EcY5082 (FM5/pKMY287) or EcY5236 (FM5/pKMY336) cells.

For the conversion as illustrated in Part A, EcY5082 (FM5/pKMY287) or EcY5236 (FM5/pKMY336) cells were grown in L-broth and induced with heat as described in Example 12. The mixture is incubated for a period sufficient to effect the bioconversion of indole to indigo. The indigo may be isolated from the cell mixture according to the procedure of Part A.

EXAMPLE 16

Mapping and Nucleotide Sequence Analysis of tmoABCDEF Gene Cluster

A. Mapping

The region of the ~10.2 kb SacI fragment (see Example 10) encoding TMO proteins was determined by deletion mapping. Deletion mapping was accompanied by DNA sequencing to reveal restriction sites. Various regions of the SacI fragment (FIGS. 3 and 4) were cloned individually into the E. coli expression vector pCFM1146 (Example 7) which can express foreign genes from a heat-inducible phage $P_L$ promoter. Each of the recombinant plasmids was introduced into the E. coli strain FM5, which contains the integrated phage lambda repressor gene $CI_{857}$ (Sussman and Jacob, Compt. Rend. Acad. Sci. 254 1517-1519 (1962)), as described by Burnette et al., (supra). The resulting strains were assayed for TMO activity by the alternative assay described in Example 11 under induced and uninduced conditions.

The following plasmids were constructed for mapping: pMY421, pMY437, pKMY336, pMY448, pMY429, and pKMY340. Cloning of an ~2.6 kb HindIII fragment of plasmid pMY401 (Example 10) containing the tmoABCD genes (FIG. 3) into pUC19 (Yanisch-Perron et al., (supra)) produced plasmid pMY419. Substitution of the XbaI-Asp718 fragment of pKMY287

Figure 4:
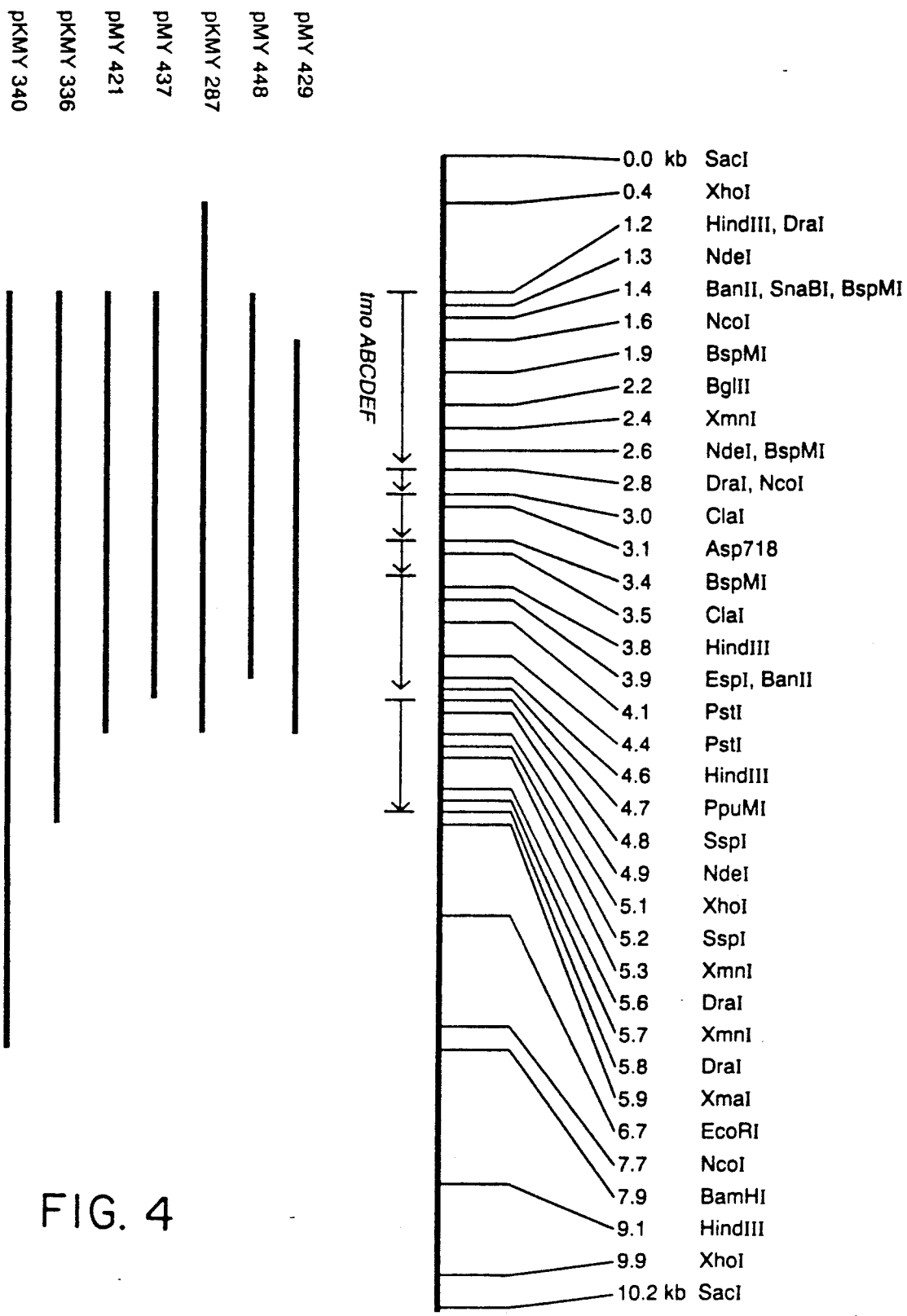
FIG. 4 illustrates a summary of recombinant plasmids and restriction maps of the PmKR1 DNA segments containing toluene monooxygenase genes. Arrows indicate transcriptional direction and sizes of the TMO genes. Heavy lines underneath the map denote the different inserts in the plasmids indicated.

(previously designated pKY287 in Example 10) with a corresponding XbaI-Asp718 fragment of pMY419 containing the tmoAB genes generated plasmid pMY421 (FIG. 4).

Several intermediate plasmids were involved in the construction of pMY437 (FIG. 4). Deletion of an ~0.9 kb SspI fragment downstream from the tmoABCDE genes in plasmid pMY401 (Example 10) produced plasmid pMY424. Insertion of a XhoI linker into the SspI site of pMY424 generated plasmid pMY436. Substitution of an Asp718-XhoI fragment of pMY421 containing the tmoDE genes with the corresponding Asp718-XhoI fragment of pMY436 generated plasmid pMY437.

Construction of plasmid pMY448 (FIG. 4) involved using the plasmids pMY476 and pKMY336. Insertion of the ~0.8 kb HindIII fragment within the tmoE gene (FIG. 4) into the SmaI site of pUC19 produced pMY476. Substitution of the Asp718-BamHI fragment of pMY421 containing the tmoDE genes with the longer Asp718-BamHI fragment of pKMY282 (previously designated pKY282 in Example 10; FIGS. 3 and 4) containing the tmoDEF genes produced plasmid pKMY336. Substitution of the EspI-BamHI fragment of pKMY336 containing part of the tmoE gene with the ~0.76 kb EspI-BamHI fragment of pMY476 produced plasmid pMY448 (FIG. 4). Deletion of an ~1.2 kb NcoI fragment from the 5' end of the tmoA gene in pKMY287 produced plasmid pMY429 (FIG. 4).

Construction of plasmid pKMY340 involved using the plasmids pKMY277 (previously designated pKY277 in Example 10) and pMY421 (described above). Deletion of an ~2.3 kb BamHI fragment from the region downstream from the tmoABCDEF gene cluster in pKMY277 generated a plasmid designated pKMY280 (previously designated pKY280 in Example 10). Replacement of the ~2 kb Asp718-BamHI fragment of pMY421 containing the tmoDE genes with the ~4.8 kb Asp718-BamHI fragment of pKMY280 containing the tmoDEF genes produced pKMY340.

Inducible TMO activity (as measured by the alternative assay described in Example 11) was observed from a strain carrying any of the recombinant plasmids pKMY287 (Example 10), pMY437, pMY421, pKMY336 or pKMY340, but not from the strain carrying pMY429 or pMY448 (FIG. 4, Table III). This result further demonstrated transcriptional direction of the TMO genes and defined more precisely the minimal DNA region required for TMO activity. The TMO genes are transcribed from left to right based on the map shown in FIG. 4. Plasmids pKMY287, pMY437 and pMY421 gave similar levels of TMO activity (Table III). Plasmids pKMY336 and pKMY340, each carrying the tmoF gene, along with the tmoABCDE genes gave enhanced levels of TMO activity (Table III). Among the recombinant plasmids yielding inducible TMO activity, pMY437 carries the smallest insert (FIG. 4). This insert is an ~3.6 kb fragment defined by the recognition sites of HindIII and SspI (FIG. 4). The essential TMO genes are therefore located between these two sites on the ~10.2 kb SacI fragment.

There is a perfect correlation between the presence of TMO activity and the indigo-producing capability among these strains tested. Indigo was produced only in strains having TMO activity but not in strains lacking TMO activity (Tables I and III). The indigo-plus strains all contain the intact tmoABCDE gene cluster and each of the indigo-minus strains misses an essential TMO component gene. Indigo production can therefore serve as a good indicator for the presence of the TMO gene cluster when these genes are investigated.

TABLE III

TMO Activities and Indigo-Forming Properties of Recombinant E. coli Plasmids Carrying Different PmKR1 DNA Fragments.

| Plasmid[a] | Specific Activity of TMO[b] (nmole min$^{-1}$ mg$^{-1}$) | Indigo Formation[c] |
|---|---|---|
| pCFM1146, Induced | 0.1 | — |
| pMY429, Uninduced | 0.1 | — |
| pMY429, Induced | 0.1 | — |
| pMY448, Uninduced | 0.1 | — |
| pMY448, Induced | 0.1 | — |
| pKMY287, Uninduced | 2.0 | + |
| pKMY287, Induced | 7.0 | + |
| pMY437, Uninduced | 0.5 | + |
| pMY437, Induced | 7.3 | + |
| pMY421, Uninduced | 0.9 | + |
| pMY421, Induced | 10.0 | + |
| pKMY336, Uninduced | 0.6 | + |
| pKMY336, Induced | 19.0 | + |
| pKMY340, Uninduced | 0.7 | + |
| pKMY340, Induced | 20.0 | + |

[a]Each plasmid listed except pCFM1146 is the E. coli expression vector pCFM1146 carrying TMO genes. The different inserts in these plasmids are defined in FIG. 4.
[b]TMO specific activities in toluene-induced and uninduced PmKR1 cells are 30 and 0.5 nmole of non-volatile material formation from toluene per minute per mg of protein, respectively.
[c]+, indigo formation; —, absence of indigo formation

B. Sequencing

Initially, the XhoI-XhoI DNA region extending from coordinate 0.4 to 5.1 on the map shown in FIG. 4 was sequenced in its entirety in both orientations. The nucleotide sequence of this XhoI fragment carrying the TMO genes was determined by the dideoxy method of Sanger et al., Proc. Natl. Acad. Sci. 74: 5463-67 (1977) on double-stranded DNA using the Sequenase ™ DNA sequencing kit obtained from United States Biochemical Corporation, Cleveland, Ohio 44122. DNA samples were denatured in 0.2 M NaOH for 10 minutes and neutralized with 0.2 M ammonium acetate (pH 4.5) before use in the sequencing reactions. The ~4.7 kb XhoI fragment and various deletion derivatives were cloned into pUC19 or pUC18 (Yanisch-Perron et al., (supra)) for DNA sequencing. Both commercially available and synthetic primers were used for sequencing reactions. The nucleotide sequence corresponding to the HindIII-SspI region required to give TMO activity is presented in FIG. 5. Five open reading frames were identified in this region.

Each of the five open reading frames was confirmed by determining the N-terminal amino acid sequence of the corresponding gene product produced in E. coli from plasmid pMY421 (see Table VI in Example 18 below) and by cloning each of the regions containing an open reading frame and demonstrating corresponding activity (see Example 17 below). The genes defined by these five open reading frames were designated tmoA, tmoB, tmoC, tmoD and tmoE in the order of transcription (FIG. 4). Part of a sixth open reading frame was also detected near the 3' end of the XhoI fragment. This led to further sequence analysis of the region downstream of the tmoABCDE gene cluster. The sequence of the entire sixth open reading frame is also shown in FIG. 5. This sixth open reading frame was designated tmoF, continuing in the order of transcription. This open reading frame was confirmed by determining the N-terminal amino acid sequence of the corresponding gene product in E. coli from plasmid pMY440 (see Table VI in Example 18 below). Plasmid pMY440 encodes the sixth open reading frame and expresses a functional TmoF protein in the *E. coli* FM5 host cells. It was constructed by deleting the ~3.4 kb HindIII fragment from the 5' end of the tmoABCDEF gene cluster in pKMY336.

The TMO genes are organized as a very closely-spaced cluster. In addition to the Shine-Delgarno (S-D) sequence (Nature 254: 34–38 (1975)) preceding each gene, only very short non-coding regions separate the genes (FIG. 5). Downstream from the tmoABCDE gene cluster, there is a GC-rich region of dyad symmetry followed by a series of thymidine residues (FIG. 5), a structure characteristic of a rho-independent transcription terminator (Platt, *Ann. Rev. Biochem.* 55: 339–372 (1986)). However, further downstream, is a sixth open reading frame encoding TmoF. The fact that the plasmids pKMY336 and pKMY340 gave higher TMO activity than did the other plasmids as shown above in Table III (Part A of this Example) indicates transcriptional read-through at the termination region described above.

The base composition of the tmoABCDEF cluster is unusual for *P. mendocina* genes. The G+C content of the DNA fragment presented in FIG. 5 is 48.8%. This low value is significantly different from the reported G+C content of 62.8–64.3% for the *P. mendocina* genome (Palleroni, et al., *J. Gen. Michrobiol,* 60: 215–231 (1970)). Consistent with the low G+C content, there is no codon usage preference for guanine and cytosine at the third position of each codon in the TMO genes (Table IV). The PmKR1 stain, initially typed as described in Whited (supra), has been retyped and the identity of this strain has been confirmed. A simple explanation of the low G+C content of the TMO genes is that these genes originated from another bacterial species, that were later transferred into *P. mendocina* on a plasmid. Consistent with such a hypothesis is the observation that the toluene utilizing property can be transferred from PMKR1 to *P. putida* KT2440. This observation suggested the presence of the toluene plasmid pAUT1 (Table I of Example 11) in PmKR1.

TABLE IV

| Codon Usage of the tmoABCDEF Genes. | | | | | | | |
|---|---|---|---|---|---|---|---|
| Amino Acid | Codon | A | B | C | D | E | F | Total |
| Gly | GGG | 4 | 0 | 1 | 0 | 1 | 9 | 15 |
| Gly | GGA | 5 | 0 | 3 | 3 | 1 | 5 | 17 |
| Gly | GGU | 14 | 1 | 3 | 2 | 5 | 6 | 31 |
| Gly | GGG | 10 | 1 | 4 | 1 | 1 | 3 | 20 |
| Glu | GAG | 15 | 5 | 5 | 2 | 14 | 12 | 53 |
| Glu | GAA | 24 | 3 | 7 | 10 | 12 | 17 | 73 |
| Asp | GAU | 19 | 5 | 5 | 5 | 13 | 8 | 55 |
| Asp | GAC | 15 | 1 | 3 | 2 | 6 | 4 | 31 |
| Val | GUG | 4 | 4 | 1 | 2 | 3 | 10 | 24 |
| Val | GUA | 5 | 3 | 4 | 1 | 3 | 6 | 22 |
| Val | GUU | 9 | 6 | 0 | 2 | 1 | 3 | 21 |
| Val | GUC | 4 | 1 | 3 | 0 | 5 | 5 | 18 |
| Ala | GCG | 7 | 2 | 1 | 1 | 3 | 9 | 23 |
| Ala | GCA | 18 | 2 | 1 | 3 | 5 | 7 | 36 |
| Ala | GCU | 7 | 2 | 1 | 5 | 10 | 6 | 31 |
| Ala | GCC | 12 | 1 | 2 | 1 | 5 | 5 | 26 |
| Arg | AGG | 1 | 0 | 0 | 1 | 2 | 1 | 5 |
| Arg | AGA | 1 | 1 | 0 | 0 | 1 | 1 | 4 |
| Ser | AGU | 4 | 0 | 2 | 0 | 10 | 3 | 19 |
| Ser | AGC | 8 | 1 | 3 | 1 | 7 | 1 | 21 |
| Lys | AAG | 14 | 1 | 2 | 0 | 8 | 7 | 32 |
| Lys | AAA | 11 | 2 | 3 | 3 | 7 | 11 | 37 |
| Asn | AAU | 8 | 2 | 2 | 3 | 7 | 9 | 31 |
| Asn | AAC | 9 | 1 | 2 | 3 | 6 | 7 | 28 |
| Met | AUG | 21 | 4 | 3 | 3 | 12 | 8 | 51 |
| Ile | AUA | 3 | 1 | 0 | 1 | 1 | 1 | 7 |
| Ile | AUU | 7 | 0 | 4 | 3 | 7 | 11 | 32 |
| Ile | AUC | 14 | 1 | 4 | 6 | 2 | 4 | 31 |
| Thr | ACG | 4 | 0 | 1 | 0 | 3 | 3 | 11 |
| Thr | ACA | 4 | 0 | 3 | 3 | 3 | 2 | 15 |
| Thr | ACU | 3 | 2 | 1 | 1 | 4 | 5 | 16 |
| Thr | ACC | 11 | 1 | 2 | 2 | 5 | 3 | 24 |
| Trp | UGG | 22 | 0 | 2 | 0 | 13 | 2 | 39 |
| End | UGA | 1 | 0 | 0 | 0 | 1 | 0 | 2 |
| Cys | UGU | 1 | 1 | 3 | 0 | 1 | 2 | 8 |
| Cys | UGC | 3 | 0 | 2 | 0 | 3 | 5 | 13 |
| End | UAG | 0 | 1 | 0 | 0 | 0 | 0 | 1 |
| End | UAA | 0 | 0 | 1 | 1 | 0 | 1 | 3 |
| Tyr | UAU | 14 | 0 | 1 | 1 | 6 | 6 | 28 |
| Tyr | UAC | 8 | 1 | 3 | 1 | 8 | 4 | 25 |
| Leu | UUG | 10 | 1 | 0 | 4 | 10 | 4 | 29 |
| Leu | UUA | 2 | 1 | 3 | 1 | 1 | 4 | 12 |
| Phe | UUU | 12 | 3 | 1 | 2 | 4 | 11 | 33 |
| Phe | UUC | 12 | 2 | 2 | 2 | 4 | 6 | 28 |
| Ser | UCG | 4 | 1 | 0 | 0 | 4 | 6 | 15 |
| Ser | UCA | 3 | 1 | 0 | 0 | 4 | 6 | 14 |
| Ser | UCU | 4 | 0 | 1 | 0 | 2 | 2 | 9 |
| Ser | UCC | 4 | 1 | 2 | 1 | 3 | 5 | 16 |
| Arg | CGG | 2 | 2 | 0 | 1 | 1 | 1 | 7 |
| Arg | CGA | 0 | 1 | 0 | 1 | 3 | 2 | 7 |
| Arg | CGU | 15 | 3 | 0 | 1 | 6 | 7 | 32 |
| Arg | CGC | 7 | 0 | 1 | 3 | 6 | 1 | 18 |
| Gln | CAG | 14 | 1 | 2 | 5 | 11 | 5 | 38 |
| Gln | CAA | 7 | 1 | 0 | 1 | 7 | 4 | 20 |
| His | CAU | 9 | 2 | 3 | 1 | 3 | 4 | 22 |
| His | CAC | 6 | 1 | 2 | 0 | 10 | 1 | 20 |
| Leu | CUG | 9 | 1 | 1 | 2 | 15 | 11 | 39 |
| Leu | CUA | 3 | 1 | 1 | 1 | 3 | 6 | 15 |
| Leu | CUU | 7 | 1 | 1 | 0 | 8 | 5 | 22 |
| Leu | CUC | 4 | 0 | 1 | 1 | 1 | 6 | 13 |
| Pro | CCG | 9 | 0 | 1 | 3 | 5 | 7 | 25 |
| Pro | CCA | 5 | 3 | 1 | 1 | 5 | 4 | 19 |
| Pro | CCU | 5 | 1 | 1 | 0 | 2 | 5 | 14 |
| Pro | CCC | 4 | 0 | 1 | 0 | 5 | 2 | 12 |

EXAMPLE 17

Identification of tmoABCDE as Essential TMO Genes

A. Plasmid pKMY341 and Single-gene Mutant Derivatives

To determine if each of the designated tmoABCDE genes as described in Example 16 encodes a TMO protein component necessary for TMO activity, a single mutation was introduced into each of the genes and its effect on TMO activity was determined. A plasmid, pKMY341, was initially constructed by cloning the tmoABCDE genes into the *E. coli* plasmid T7-5, followed by introducing a DNA sequence change into the individual genes. The pT7-5 plasmid is a ColEI-based plasmid containing the β-lactamase gene and a multiple cloning site downstream from a T7 RNA polymerase-specific promoter obtained from S. Tabor (see, e.g., Tabor and Richardson, *Proc. Natl. Acad. Sci.* 82: 1074–1078 (1985)).

The plasmid pKMY341 carrying the tmoABCDE genes was constructed by cloning the ~4.7 kb XbaI-BamHI fragment of pKMY336 (Example 16) into the XbaI and BamHI sites of pT7-5. The plasmids pMY459, pMY458, pMY482, pMY484, and pMY472 carry mutations in the tmoA, tmoB, tmoC, tmoD, tmoE genes, respectively. Cleavage of the NcoI site in the tmoA gene (FIG. 4) of pKMY341 followed by end-filling and ligation generated plasmid pMY459. The same treatment at the NcoI site in the tmoB gene, at the Asp718 site in the tmoC gene, and at the ClaI site in the tmoD gene, generated the mutations in plasmids pMY458, pMY482, and pMY484, respectively (FIG. 4). Cleavage of the BanII site in the tmoE gene (FIG. 4) followed by removing the overhangs and ligation generated the mutation in plasmid pMY472.

Enyzme assays revealed that each of the mutations completely eliminated TMO activity in *E. coli* cells as shown in Table V.

TABLE V

Complementation Between Individually Cloned tmo Genes and the tmoABCDE Gene Cluster Carrying Corresponding Mutations.

| Bacterial Strain (EcY#)[a] | Plasmid[b] | tmo Genes | Specific Activity of TMO (nmole min$^{-1}$ mg$^{-1}$) |
|---|---|---|---|
| 5246 | pKMY341 | ABCDE | 10.7 |
| 5283 | pMY459 | A$^-$BCDE | 0.06 |
| 5282 | pMY458 | AB$^-$CDE | 0.04 |
| 5286 | pMY482 | ABC$^-$DE | 0.08 |
| 5287 | pMY484 | ABCD$^-$E | 0.05 |
| 5285 | pMY472 | ABCDE$^-$ | 0.10 |
| 5258 | pMY438 | A | 0.09 |
| 5265 | pMY447 | B | 0.03 |
| 5288 | pMY474 | C | 0.04 |
| 5289 | pMY479 | D | 0.02 |
| 5224 | pKMY327 | E | 0.04 |
| 5291 | pMY438, pMY459 | A, A$^-$BCDE | 2.0 |
| 5290 | pMY447, pMY458 | B, AB$^-$CDE | 3.9 |
| 5297 | pMY474, pMY482 | C, ABC$^-$DE | 7.4 |
| 5298 | pMY479, pMY484 | D, ABCD$^-$E | 2.0 |
| 5292 | pKMY327, pMY472 | E, ABCDE$^-$ | 10.3 |

[a]Each of the strains was constructed by introducing an appropriate plasmid or plasmids into the *E. coli* strain HB101. All cultures were grown in the presence of 0.35 mM sodium salicylate which induced the TMO genes cloned into pKMY319.
[b]Construction of all plasmids is described in Examples 16 and 17.

B. Complementation Tests Between Mutant Derivatives of Plasmid pKMY341 and Plasmids carrying a Single TMO Gene To determine whether lack of TMO activity was due to lack of expression of the TMO genes in the presence of a polar mutation which itself is not located in a TMO gene, complementation tests between plasmids pMY459, pMY458, pMY482, pMY484 and pMY472 (constructed as described in part A above) and plasmids carrying only one of the tmoABCDE genes were conducted. Plasmids pMY438, pMY447, pMY474, pMY479, and pKMY327 were constructed to contain the tmoA, B, C, D, and F genes, respectively, in the broad host range expression vector pKMY319. Plasmid pKMY319 is described and claimed in co-pending and co-assigned U.S. patent application Ser. No. 07/590,280, filed on Sep. 28, 1990, hereby incorporated by reference in its entirety. Plasmid pKMY319 is a plasmid vector in which expression of foreign genes can be regulated by the NahR protein and an inducer, such as sodium salicylate.

Plasmids pMY438, pMY447, pMY474, pMY479, and pMY327 are derivatives of pKMY319 that carry tmoA, tmoB, tmoC, tmoD, and tmoE, respectively, and were constructed as follows. For the construction of plasmid pMY438, pMY430 was initially constructed by cloning an ~1.6 kb DraI fragment containing the tmoA gene (FIG. 4) into the SmaI site of pUC19 in an orientation that placed the XbaI site of pUC19 at the 5' end of the tmoA gene. Plasmid pMY438 was constructed by cloning the ~1.6 kb XbaI-SacI fragment of pMY430 carrying the tmoA gene into the XbaI and SacI sites of pKMY319.

Plasmids pKMY332 and pMY446 were used in the construction of pMY447. The plasmid pKMY332 was obtained by deleting an ~2 kb HpaI-XmnI fragment of pKMY287 at the 5' end of the TMO gene cluster (FIG. 4). Cloning of an ~0.7 kb XbaI-Asp718 fragment of pKMY332 containing the tmoB gene into the XbaI and Asp718 sites of the pKMY319 produced plasmid pMY446. Further deletion of an ~0.2 kb XbaI-NdeI fragment upstream from the tmoB gene in pMY446 (FIG. 4) generated plasmid pMY447.

Construction of plasmid pMY474 involved constructing intermediate plasmids pMY414, pMY426, pMY452, and pMY466. Cloning of an ~0.4 kb Asp718-ClaI fragment of pKMY282 containing the 3' end portion of the tmoC gene (FIG. 4) into the Asp718 and AccI sites of pUC19 produced intermediate plasmid pMY414. Deletion of an ~0.1 kb BspMI-SphI fragment downstream from the tmoC gene (FIG. 4) generated intermediate plasmid pMY426. Ligation of a SacI linker to an end-filled HindIII site in pMY426 and insertion of the Asp718-SacI fragment of pMY426 into pKMY319 generated intermediate plasmid pMY452. Cloning of an ~1.9 kb ClaI-Asp718 fragment of pKMY341 containing the tmoAB genes and the 5' end of the tmoC gene (FIG. 4) into the ClaI and Asp718 sites of pMY452 produced intermediate plasmid pMY466. Deletion of a 1.8 kb ClaI fragment upstream from the tmoC gene in pMY466 generated plasmid pMY474.

Intermediate plasmids pMY404, pMY470, and pMY478 were generated and used in the construction of plasmid pMY479. Cloning of the ~4.7 kb BamHI-SphI fragment of pMY401 carrying the tmoABCDE genes into the plasmid pUC18 (Yanisch-Perron et al., (supra)) produced intermediate plasmid pMY404 (see Example 10). Deletion of the ~3 kb BspMI fragment of pMY404 carrying the tmoABC genes (FIG. 4) generated intermediate plasmid pMY470. An ~0.4 kb HindIII fragment of pMY470 carrying the tmoD gene (FIG. 4) was end-filled and ligated along with another end-filled 0.8 kb HindIII fragment of pMY470 into the SmaI site of pUC19 (Yanisch-Perron et al., (supra)) to form intermediate plasmid pMY478. In pMY478, a NheI site was generated upstream from the tmoD gene as a result of ligation of two end-filled HindIII sites. Cloning of the ~0.4 kb NheI-SacI fragment of pMY478 carrying the tmoD gene into the XbaI and SacI sites of pKMY319 generated plasmid pMY479.

Plasmid pKMY327 was constructed from the intermediate plasmid pKMY324. Cloning of the XhoI fragment of pKMY282 carrying the tmoABCDE genes into pKMY319 produced intermediate plasmid pKMY324. Deletion of an ~3.1 kb ClaI fragment of pKMY324 upstream from the tmoE gene (FIG. 4) generated plasmid pKMY327.

Each of these plasmids was introduced by transformation into a strain which contained a corresponding member of the plasmids pMY459, pMY458, pMY482, pMY484, and pMY472 and the TMO activity in each of the resulting strains was determined after induction as shown in Table V above. A plasmid carrying a mutation in any member of the tmoABCDE genes was complemented by the plasmid which carries that particular gene in synthesizing the TMO enzyme (Table V). This result demonstrated that the mutation in each of the tmo genes, did not abolish the expression of the downstream tmo genes. Since each of the mutations prevented the synthesis of a functional TMO system (Table V), this indicated that each of the tmoABCDE genes plays an essential role in directing the synthesis of the TMO enzyme system.

EXAMPLE 18

Purification and Analysis of TMO Proteins

TMO proteins except TmoF were partially purified from PMKR1 or *E. coli* FM5 cells carrying the plasmid pMY421 by DEAE cellulose chromatography according to Whited, (supra), except that TEGD buffer (50 mM Tris, pH 7.45; 10% glycerol; 10% ethanol; mM dithiothreitol) instead of PEG buffer was used in the column. The TmoF protein was purified from *E. coli* FM5 cells carrying the plasmid pMY440, by isolating the protein after polyacrylamide gel electrophoresis of the FM5/pMY440 lysate.

Sodium dodecyl sulfate polyacrylamide gel electrophoresis (SDS-PAGE) was performed essentially according to Laemmli, *Nature* 227: 680-685 (1970). Protein samples were heated at 65° C. for 15 minutes in a loading buffer containing 2% SDS, 5% 2-mercaptoethanol, 10% glycerol, 0.02% bromophenol blue, and 62.5 mM Tris-Cl (pH 6.8) before they were loaded on the gel.

For determination of N-terminal amino acid sequences, partially purified TMO proteins were further purified by SDS-PAGE and electroblotted onto polyvinyldifluoride membrane according to Matsudaira, *J. Biol. Chem.* 262: 10035-38 (1987) with slight modifications. The protein bands immobilized on the polyvinyldifluoride membrane were visualized by Coomassie blue staining and destained with 50% methanol and 7% acetic acid. The stained bands were excised with a razor blade and sequenced in an Applied Biosystems Model 477 automated protein sequencer as described by Lu et al., *Int. J. Peptide Protein Res.* 33: 237-49 (1989).

Conditions to generate tryptic fragments were described by Klein et al., *Arch. Biochem. Biophus.* 276: 531-537 (1990). The tryptic peptides were isolated by reverse-phase HPLC in an acetonitrile-trifluoroacetic acid gradient elution system. The isolated peptides were pooled and loaded onto a glass-fiber disc precycled with polybrene for automatic sequence analysis. In situ cyanogen bromide cleavage of protein samples and sequence analysis of the cleaved mixture were also described by Klein et al., (supra).

The N-terminal amino acid sequences of the tmoA, B, C, D, F and gene products are shown in Table VI. These N-terminal amino acid sequences for each of the TmoA, B, C, D and E proteins encoded by the HindIII-SspI region and by the HindIII-XmaI region for the TmoF protein (as described in Example 16 and Table IV) agrees completely with that predicted from the nucleotide sequence of the corresponding open reading frame (FIG. 5). The estimated molecular weights of the purified TmoA, B, C, D, E and F proteins are also shown in Table VI, along with their predicted molecular weights based on the nucleotide sequence of the tmoA, B, C, D, E and F genes shown in FIG. 5. The observed and expected protein molecular weights correlate closely for the tmoA,B,C,D, and E gene products, but not for the tmoC gene product. The nucleotide sequence of the tmoC gene has capacity to encode a protein with a molecular weight of approximately 12,000 as shown in Table VI. However, on SDS-PAGE the observed molecular weight of the TmoC protein was approximately 25,000 (Table VI), almost exactly twice the size of the expected molecular weight. A 25 kilodalton (kDa) protein was also isolated from PMKR1 and identified to be the same 25 kDa tmoC product isolated from the recombinant *E. coli* by comparing the N-terminal amino acid sequences. Further characterization of the 25 kDa protein demonstrated that it is encoded solely by the tmoC gene. This protein was isolated from *E. coli* and further purified from SDS polyacrylamide gels. Fragments of the protein were obtained in separate experiments after trypsin digestion or cyanogen bromide treatment. N-terminal amino acid sequence analysis demonstrated that all of the fragments were cleavage products of the TmoC protein. This result suggested that the 25 dKa protein was a dimer of the tmoC product not fully reduced under the conditions used for the SDS-PAGE.

TABLE VI

N-terminal Sequence and Molecular Weights of the tmoABCDEF Gene Products Produced from Recombinant *E. coli* FM5 Host Cells Carrying Plasmid pMY421[a] or pMY440[b]

| Gene | Region of Nucleotide Sequence | Product Molecular Weight Predicted From Nucleotide Sequence | Estimated From Purified Protein | N-terminal Sequence Determined From Purified Protein[c] |
|---|---|---|---|---|
| tmoA[a] | 37–1536 | 57,982 | 55,000 | AMHPRKXDWYELTR |
| tmoB[a] | 1558–1809 | 9,588 | 9,500 | SAFPVHAAFEXDFLVQLVV VDLNDSMDQVA |
| tmoC[a] | 1818–2153 | 12,326 | 25,000 | SFEKIXSLDDIWVGEMETFETS |
| tmoD[a] | 2217–2525 | 11,618 | 11,500 | STLADQALHNNNVGPIIR IIRAGD |
| tmoE[a] | 2539–3519 | 38,386 | 35,000 | SFESKXPMRTWSXL |
| tmoF[b] | 3548–4575 | 35,983 | 38,000 | MFNIQSDDLLHHFE |

[c]The letter X indicates undetermined amino acid.

The definitive functions of each of the TMO genes is not known. However, there is evidence at least to suggest a role for the tmoC gene. Comparison of the amino acid sequences deduced from the TMO genes with those of known proteins reveal homology between the tmoC product and several other ferredoxin proteins functioning in dioxygenase systems. Among the 114 amino acid residues in the TmoC protein, 36 residues (31.6%) are identical to those of the benzene dioxygenase ferredoxin protein at corresponding positions and 14 residues (12.3%) are represented by evolutionarily related amino acids in the benzene dioxygenase ferredoxin at corresponding positions (FIG. 6). Similar homology exists between the TmoC protein and the naphthalene dioxygenase ferredoxin protein (FIG. 6). The ferredoxin component of the toluene dioxygenase system from PpFI differs from the benzene ferredoxin protein by only six amino acid residues (Zylstra and Gibson, *J. Biol. Chem.* 264: 14940–46 (1989)). It therefore shares similar homology with the TmoC protein. The region of maximum homology between the TmoC protein and the other ferredoxins is located between positions 53 and 77 (FIG. 6). Among the 23 amino acid residues in this region, the TmoC protein shares 10 (43%) with the benzene dioxygenase ferredoxin and 9 (39%) with the naphthalene dioxygenase ferredoxin (FIG. 6). In addition, the two dioxygenase ferredoxins share 13 (56.5%) amino acids in this region (FIG. 6). It is interesting to note that this region contains two conserved cysteine residues (at positions 53 and 74, respectively) each of which is followed by a conserved histidine in the vicinity. Benzene dioxygenase ferredoxin (Geary et al., (supra)) and toluene dioxygenase ferredoxin (Subramanian et al., *J. Biol. Chem.* 260: 2355–63 (1985)), each contains a single [2Fe-2S] cluster with a redox potential significantly higher than [2Fe-2S] clusters coordinated to four cysteine residues. It has been suggested by Cline et al., *J. Biol. Chem.* 260: 3251–54 (1985), that in addition to cysteines, histidine residues may provide nitrogen ligands to the [2Fe-2S] cluster which may contribute to the higher redox potential of the cluster. It is likely that this region of maximum homology between the two dioxygenase ferredoxins is involved in the binding of the [2Fe-2S] cluster. The fact that the TmoC protein shares overall homology with these two ferredoxins and does so especially in this region suggests that it is a ferredoxin of the toluene monooxygenase system.

EXAMPLE 19

Degradative Bioconversion of TCE by Microorganism Host cells Containing Recombinant Plasmids Carrying PmKRI Toluene Monooxygenase Genes TCE degradation catalyzed by the toluene monooxygenase of PMKR1 has been demonstrated by Winter et al., Bio/Technology 1: 282-285 (1989) and claimed in co-assigned U.S. patent application Ser. No. 177,640 incorporated by reference. Plasmid pKMY342 is plasmid pKMY319 carrying two copies of the tmoABCDEF gene cluster and is described in co-pending and co-assigned U.S. patent application Ser. No. 07/590,280 filed Sep. 28, 1990. It gives higher TMO activity that the recombinant plasmids previously described for TCE degradation and can replicate in all Gram-negative bacteria tested to date. It is therefore a particularly preferred and improved plasmid for use in TCE degradation. Other recombinant plasmids such as pKMY336 and pKMY340 (Example 16) that give higher TMO activity than the plasmids described in U.S.S.N. 177,640 are also useful for TCE degradation.

In a particularly preferred embodiment, *Pseudomonas putida* Y2511 cells harboring recombinant plasmid pKMY342 are grown to mid-log phase in L-broth with 0.35 mM sodium salicylatic as inducer. The cells are washed in L-broth for the degradative bioconversion of TCE, as follows. Cells are resuspended to an $OD_{550}$ of ~0.5 in L-broth, and 4 ml of the cell suspension is added to serum vials. TCE (Aldrich, (Milwaukee, Wis.), spectrophotometric grade) is diluted in N,N-dimethylformamide (DMF) (Aldrich, spectrophotometric grade) to 10 mM or 20 mM and 4 μl added to cell suspension to give a final TCE concentration of 10 μM (1.3 ppm) or 20 μM (2.6 ppm). Vials are stoppered, vortexed, and 10 μl of gas phase are withdrawn using a gas-tight syringe at various times for analysis. Gas phase samples are analyzed on a Hewlett-Packard 5890A gas chromatograph equipped with a 25 meter 5% phenyl methyl silicone column (Hewlett Packard, Palo Alto, Calif.) and a $^{63}$Ni electron capture detector. The injector, oven, and detector temperatures are 120°, 100°, and 300°, respectively. The carrier gas is helium and the makeup gas is 95% argon-5% methane. Peak areas are calculated by a Hewlett-Packard 3392A Integrator. Data are reported as the percentage of TCE remaining at various times after addition to the cell suspension. The amount of TCE present at zero time is taken to be 100%.

What is claimed is:

1. An isolated nucleotide sequence selected from the group consisting of, a nucleotide sequence encoding the tmoABCDE gene complex derived from *Pseudomonas* and, a nucleotide sequence which hybridizes to said tmoABCDE gene complex and which encodes a protein possessing toluene monooxygenase active.

2. An isolated nucleotide sequence selected from the group consisting of, a nucleotide sequence encoding the tmoABCDEF gene complex derived from *Pseudomonas* and, a nucleotide sequence which hybridizes to said tmoABCDEF gene complex and which encodes a protein possessing toluene monooxygenase activity.

3. A recombinant plasmid comprising a nucleotide sequence encoding a tmoABCDE gene complex of claim 1.

4. A recombinant plasmid comprising a nucleotide sequence encoding a tmoABCDEF gene complex of claim 2.

5. The recombinant plasmid of claim 4 wherein said plasmid comprising a DNA segment which encodes a Tmo protein selected from the group consisting of TmoA, TmoB, TmoC, TmoD, TmoE, and TmoF 6. A recombinant plasmid according to claim 5, wherein the toluene monooxygenase gene encodes a Tmo A protein.

7. A recombinant plasmid according to claim 5, wherein the toluene monooxygenase gene encodes a TmoB protein.

8. A recombinant plasmid according to claim 5, wherein the toluene monooxygenase gene encodes a TmoC protein.

9. A recombinant plasmid according to claim 5, wherein the toluene monooxygenase gene encodes a TmoD protein.

10. A recombinant plasmid according to claim 5, wherein the toluene monooxygenase gene encodes a TmoE protein.

11. A recombinant plasmid according to claim 5, wherein the toluene monooxygenase gene encodes a TmoF protein.

12. A microorganism host cell transformed with the recombinant plasmid according to claim 3.

13. A microorganism host cell transformed with the recombinant plasmid according to claim 4.

14. A microorganism host cell transformed with the recombinant plasmid according to claim 5.

15. A microorganism host cell transformed with the recombinant plasmid according to claim 6.

16. A microorganism host cell transformed with the recombinant plasmid according to claim 7.

17. A microorganism host cell transformed with the recombinant plasmid according to claim 8.

18. A microorganism host cell transformed with the recombinant plasmid according to claim 9.

19. A microorganism host cell transformed with the recombinant plasmid according to claim 10.

20. A microorganism host cell transformed with the recombinant plasmid according to claim 11.

21. A DNA sequence encoding the amino acid sequences set forth in FIG. 5.

22. A DNA sequence encoding the tmoABCDEF genes as set forth FIG. 5.

* * * * *